US009969795B2

(12) United States Patent
Beaumont et al.

(10) Patent No.: US 9,969,795 B2
(45) Date of Patent: May 15, 2018

(54) MEANS AND METHODS FOR PRODUCING HIGH AFFINITY ANTIBODIES

(71) Applicant: AIMM THERAPEUTICS B.V., Amsterdam (NL)

(72) Inventors: Tim Beaumont, Ouderkerk a/d Amstel (NL); Mark Jeroen Kwakkenbos, Amsterdam (NL); Hergen Spits, Amsterdam (NL); Adrianus Quirinus Bakker, Hoorn (NL); Koen Wagner, Leiden (NL)

(73) Assignee: AIMM THERAPEUTICS B.V., Amsterdam (NL)

( * ) Notice: Subject to any disclaimer, the term of this patent is extended or adjusted under 35 U.S.C. 154(b) by 0 days. days.

(21) Appl. No.: 14/956,919

(22) Filed: Dec. 2, 2015

(65) Prior Publication Data
US 2016/0096881 A1    Apr. 7, 2016

Related U.S. Application Data

(63) Continuation of application No. 13/990,988, filed as application No. PCT/EP2011/071676 on Dec. 2, 2011, now Pat. No. 9,206,247.

(60) Provisional application No. 61/419,909, filed on Dec. 6, 2010.

(30) Foreign Application Priority Data

Dec. 2, 2010   (EP) .................................... 10193562

(51) Int. Cl.
*C07K 16/00*   (2006.01)
*C07K 16/10*   (2006.01)
*C07K 14/47*   (2006.01)

(52) U.S. Cl.
CPC ...... *C07K 16/1018* (2013.01); *C07K 14/4703* (2013.01); *C07K 14/4747* (2013.01); *C07K 16/00* (2013.01); *C07K 2317/21* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,997,764 A | 3/1991 | Dalla Favera | |
| 5,684,147 A | 11/1997 | Agrawal et al. | |
| 5,849,900 A | 12/1998 | Moelling | |
| 5,866,757 A | 2/1999 | Reisner | |
| 6,001,558 A | 12/1999 | Backus et al. | |
| 7,378,276 B2 | 5/2008 | Ettinger et al. | |
| 7,964,406 B2 | 6/2011 | Spits et al. | |
| 8,247,228 B2 | 8/2012 | Ettinger et al. | |
| 8,318,487 B2 | 11/2012 | Spits et al. | |
| 8,389,235 B2 * | 3/2013 | Ohmori | C07K 16/00 435/69.1 |
| 8,389,281 B2 | 3/2013 | Spits et al. | |
| 8,999,707 B2 * | 4/2015 | Dessain | C07K 16/1282 435/326 |
| 2003/0099613 A1 | 5/2003 | Berkhout et al. | |
| 2003/0152559 A1 | 8/2003 | Yang et al. | |
| 2003/0158131 A1 | 8/2003 | Aldovini | |
| 2005/0009180 A1 | 1/2005 | Yang et al. | |
| 2005/0238626 A1 | 10/2005 | Yang et al. | |
| 2006/0167230 A1* | 7/2006 | Koga | C07K 14/8121 530/387.3 |
| 2006/0236417 A1* | 10/2006 | Sakaguchi | A01K 67/0275 800/18 |
| 2008/0274991 A1 | 11/2008 | Berkhout et al. | |
| 2008/0293068 A1 | 11/2008 | Tsien et al. | |
| 2008/0305076 A1 | 12/2008 | Ettinger et al. | |
| 2009/0093024 A1 | 4/2009 | Bowers et al. | |
| 2009/0217403 A1 | 8/2009 | Spits | |
| 2010/0093038 A1 | 4/2010 | Spits | |
| 2010/0113745 A1 | 5/2010 | Spits et al. | |
| 2010/0239593 A1 | 9/2010 | Spits et al. | |
| 2011/0020323 A1 | 1/2011 | Beaumont et al. | |
| 2012/0070446 A1 | 3/2012 | Beaumont et al. | |
| 2012/0151613 A1 | 6/2012 | Wang et al. | |
| 2012/0157662 A1 | 6/2012 | Beaumont et al. | |
| 2016/0194382 A1* | 7/2016 | Beaumont | C07K 16/00 530/389.4 |
| 2017/0009205 A1* | 1/2017 | Van Helden | C07K 16/00 |

FOREIGN PATENT DOCUMENTS

| | | |
|---|---|---|
| EP | 1627563 | 2/2006 |
| EP | 1997830 A1 | 12/2008 |
| GB | 2398783 | 9/2004 |
| JP | 2007510666 | 4/2007 |
| JP | 2008539794 | 11/2008 |
| JP | 2010528601 | 8/2010 |
| WO | 1989008146 | 9/1989 |
| WO | 1994017086 | 1/1994 |
| WO | 1994008004 | 4/1994 |
| WO | 1994027426 A1 | 12/1994 |
| WO | 1995006409 | 3/1995 |
| WO | 1996001313 | 1/1996 |
| WO | 1996018413 A1 | 6/1996 |
| WO | 2001018185 A1 | 3/2001 |
| WO | 2001020013 A3 | 3/2001 |

(Continued)

OTHER PUBLICATIONS

Ahmad et al., Mechanism of SMRT Corepressor Recruitment by the BCL6 BTB Domain, Molecular Cell, Dec. 2003, pp. 1551-1564, vol. 12.

Alajez, et al., Therapeutic potential of a tumor-specific, MHC-unrestricted T-cell receptor expressed on effector cells of the innate and the adaptive immune system through bone marrow transduction and immune reconstitution, Blood, Jun. 15, 2005, vol. 105, No. 12; pp. 4583-4589.

(Continued)

*Primary Examiner* — Michail A Belyavskyi
(74) *Attorney, Agent, or Firm* — Gianna Julian-Arnold; Saul Ewing Arnstein & Lehr LLP

(57) ABSTRACT

The invention provides means and methods for producing high-affinity antibodies against an antigen of interest, usually stable B-cell cultures.

8 Claims, 9 Drawing Sheets

(56) References Cited

FOREIGN PATENT DOCUMENTS

| WO | 2003050262 A3 | 6/2003 |
|---|---|---|
| WO | 2003052083 A3 | 6/2003 |
| WO | 2003068819 A1 | 8/2003 |
| WO | 2003070193 A2 | 8/2003 |
| WO | 2003079757 A2 | 10/2003 |
| WO | 2004083249 A3 | 12/2004 |
| WO | 2005044306 A2 | 5/2005 |
| WO | 2005052164 A1 | 6/2005 |
| WO | 2005052139 A2 | 9/2005 |
| WO | 2005102383 A1 | 11/2005 |
| WO | 2005123923 A3 | 12/2005 |
| WO | 2006016808 A3 | 2/2006 |
| WO | 2006132524 A1 | 12/2006 |
| WO | 2007058527 A2 | 5/2007 |
| WO | 2007067032 A1 | 6/2007 |
| WO | 2007067046 A1 | 6/2007 |
| WO | 2008147196 A2 | 12/2008 |
| WO | 2010018185 A1 | 2/2010 |
| WO | 2011008092 A2 | 1/2011 |
| WO | 2011008093 A1 | 1/2011 |
| WO | 2011043643 A1 | 4/2011 |
| WO | 2012072814 A1 | 6/2012 |
| WO | 2013081463 A2 | 6/2013 |

OTHER PUBLICATIONS

Boise et al., bcl-x, a bcl-2-Related Gene That Functions as a Dominant Regulator of Apoptotic Cell Death, Cell, Aug. 27, 1983, pp. 597-608, vol. 74.
Charbonneau et al., Prolongation of murine hybridoma cell survival in stationary batch culture by Bcl-Xl expression, Cytotechnology, 2000, pp. 131-139, vol. 34.
Chlewicki, et al., High-affinity, Peptide-specific T Cell Receptors can be Generated by Mutations in CDR1, CDR2 or CDR3; J. Mol. Biol.; 2005, 346, 223-239.
Clay, et al., Efficient Transfer of a Tumor Antigen-Reactive TCR to Human Peripheral Blood Lymphocytes Confers Anti-Tumor Reactivity, Journal of Immunology, 1999, pp. 507-513, vol. 163, The Williams and Wilkins Co. Baltimore, MD, US.
Clay, et al. Potential Use of T Cell Receptor Genes to Modify Hematopoietic Stem Cells for the Gene Therapy of Cancer, Pathology Oncology Research, 1999, pp. 3-15, vol. 5, No. 1, Budapest, Hungary.
Das, et al., Abstract, A Conditionally Replicating Virus as a Novel Approach Toward an HIV Vaccine, Methods in Enzymology, 2004, pp. 359-379, vol. 388, Academic Press, San Diego, US.
Das, et al., Viral evolution as a tool to improve the tetracycline-regulated gene expression system, The Journal of Biological Chemistry, Apr. 30, 2004, pp. 18776-18782, vol. 279, No. 18.
Epeldegui, et al., Infection of Human B Cells with Epstein-Barr Virus Results in the Expression of Somatic Hypermutation-Inducing Molecules and the Accrual of Oncogene Mutations, Molecular Immunology, Feb. 1, 2007, vol. 44, No. 5, Pergamon, GB.
Gil et al., Somatic Mutations and Activation-Induced Cytidine Deaminase (AID) Expression in Established Rheumatoid Factor-Producing Lymphoblastoid Cell Line, Molecular Immunology, Jan. 1, 2007, pp. 494-505, vol. 44, No. 4, Pergamon, GB.
Gimeno, et al. Monitoring the effect of gene silencing by RNA interference in human DC34<-/-> cells injected into newborn RAG2<-/-> |gamma|c <-/-> mice: Functional inactivation of p53 in developing T cells, Blood Dec. 15, 2004 United States, vol. 104 No. 13, Dec. 15, 2004, pp. 3886-3893, XP002317351, ISSN: 0006-4971, the whole document.
Goldman, et al., Enhanced human cell engraftment in mice deficient in RAG2 and the common cytokine receptor gamma chain, British Journal of Haematology, Oxford, GB, vol. 103, No. 2, Nov. 1998, pp. 335-342, XP002249529, ISSN 0007-1048, the whole document.
Gossen, et al., Abstract, Transcriptional Activation by Tetracyclines in Mammalian Cells, Science, Jun. 23, 1995, pp. 1766-1769, vol. 268, American Association for the Advancement of Science, US.
Grillot, et al., bcl-x Exhibits Regulated Expression During B Cell Development and Activation and Modulates Lymphocyte Survival in Transgenic Mice, The Journal of Experimental Medicine, Feb. 1996, pp. 381-391, vol. 183.
Jung, et al., Inducible Expression of Bcl-XL Restricts Apoptosis Resistance to the Antibody Secretion Phase in Hybridoma Cultures, Biotechnology and Bioengineering, pp. 180-187, vol. 79.
Kang, et al. Long-term expression of a T-cell receptor beta-chain gene in mice reconstituted with retrovirus-infected hematopoietic stem cells, Proc. Natl. Acad. Sci., Dec. 1990, pp. 9803-9807, vol. 87, National Academy of Science, Washington, DC, US.
Knodel, el al., Abstract, Blimp-1 over-expression abrogates IL-4- and CD40-mediated suppression of terminal B cell differentiation but arrests isotype switching, European Journal of Immunology, 2001, pp. 1972-1980, vol. 31, No. 7.
Knott, et al., Tetracycline-dependent Gene Regulation: Combinations of Transregulators Yield of a Variety of Expression Windows, Biotechniques, 2002, pp. 796-806, vol. 32, No. 4; Informa Life Sciences Publishing, Westborough, MA, US.
Kobayashi, et al., Abstract, Prevention of acute liver failure in rats with reversibly immortalized human hepatocytes; Science (Washington, DC), vol. 287, No. 5456, Feb. 18, 2000, pp. 258-1262, XP002159501, ISSN: 0036-8075.
Koff, HIV vaccine development: Challenges and opportunities towards solving teh HIV vaccine-neutralizing antibody problem; Vaccine vol. 30 (2012) pp. 4310-4315.
Kriangkum, et al., Impaired class switch recombination (CSR) in Waldenström macroglobuliemia (WM) despite apparently normal CSR machinery; Blood, 2006, v. 107, pp. 2920-2927.
Krueger, et al., Single-chain Tet Transregulators, Nucleic Acids Research, Jun. 15, 2003, pp. 3050-3056, vol. 31, No. 12 Oxford University Press, Surrey, GB.
Lee, et al., Regulation of the Germinal Center Gene Program by Interferon (IFN) Regulatory Factor 8/IFN Consensus Sequence-Binding Protein, Journal of Experimental Medicine, Jan. 2006, pp. 63-72, vol. 203, No. 1.
Lin, et al., Blimp-1-Dependent Repression of Pax-5 Is Required for Differentiation of B Cells to Immunoglobulin M-Secreting Plasma Cells, Molecular and Cellular Biology, Jul. 2002, pp. 4771-4480, vol. 22, No. 13.
Mathas, et al., Intrinsic inhibition of transcription factor E2A by HLH proteins ABF-1 and Id2 mediates reprogramming of neoplastic B cells in Hodgkin lymphoma, Nature Immunology, Feb. 2006, pp. 207-215, vol. 7, No. 2.
Mehta, et al., IL-21 Induces the apoptosis of resting and activated primary B cells, Journal of Immunology, Apr. 15, 2003, pp. 4111-4118, vol. 170, No. 8, Hie Williams and Wilkins Co., Baltimore, MD, US.
Morrison, et al.,Vectors and Approaches for the Eukaryotic Expression of Antibodies and Anitbody Fusion Proteins, Antibody Engineering, 2nd ed., Chapter 9, pp. 267-293.
Mulloy, et al. Maintaining the seif-renewai and differentiation potential of human CD34+ hematopoietic cells using a single genetic element, Blood, vol. 102, No. 13, Dec. 15, 2003, pp. 4369-4376, XP002317905, SSN: 0006-4971, the whole document.
Muramatsu, et al., Class Switch Recombination and Hypermutation Require Activation-Induced Cytidine Deaminase (AID), a Potential RNA Editing Enzyme, Cell, Sep. 1, 2000, pp. 553-563, vol. 102, No. 5.
Park, Hong-Jai, et al., Insights into the Role of Follicular Helper T Cells in Autoimmunity, Immune Network, vol. 14, No. 1: pp. 21-29, Feb. 2014.
Petrie, et al., T Cell Receptor Gene Recombination Patterns, and Mechanisms: Cell Death, Rescue, and T Cell Production, J Exp Med 1995, vol. 182, pp. 121-127.
Roughan, et al., The Intersection of Epstein-Barr Virus with the Germinal Center, Journal of Virology, Apr. 15, 2009, vol. 83, No. 3, pp. 3968-3976.
Reljic, et al., Suppression of Signal Transducer and Activator of Transcription 3-dependent B Lymphocyte Terminal Differentiation by BCL-6, J. Exp. Med., Dec. 18, 2000, vol. 192, pp. 1841-1847, Rockefeller University Press.

(56) References Cited

OTHER PUBLICATIONS

Salucci, et al., Tight control of gene expression by a helper-dependent adenovirus vector carrying the rtTA2S-M2 tetracycline transactivator and repressor systems, Gene Therapy, 2002, pp. 1415-1421, vol. 9, Macmillam Press Ltd., Basingstoke, GB.

Schaft, et al., Peptide fine specificity of anti-glycoprotein 100 CTL is preserved following transfer of engineered TCRαβ genes into primary human T lymphocytes, The Journal of Immunology, 2003, vol. 170, pp. 2186-2194.

Scheeren, et al., STAT5 regulates the self-renewal capacity and differentiation of human memory B cells and controls Bcl-6 expression, Nature Immunology, 2005, vol. 6, pp. 303-313.

Schuringa, et al., Constitutive activation of STAT5A promotes human hematopoietic stem cell self-renewal and erythroid differentiation, Journal of Experimental Medicine, vol. 200, No. 5, Sep. 6, 2004, pp. 623-635.

Schuringa, et al., Enforced Activation of STAT5A Facilitates the Generation of Embryonic Stem-Derived Hematopoietic Stem Cells That Contribute to Hematopoiesis In Vivo, Stem Cells 2004, vol. 22, pp. 1191-1204.

Sciammas, et al., Modular Nature of Blimp-1 in the Regulation of Gene Expression during B Cell Maturation, The Journal of Immunology, 2004, pp. 5427-5440, vol. 172.

Shaffer, A.L., et al., Lymphoid Malignancies: The Dark Side of B-Cell Differentiation, Nature Reviews, Immunology, vol. 2, pp. 1-13, Dec. 2002.

Shaffer, et al., Blimp-1 orchestrates plasma cell differentiation by extinguishing the mature B cell gene expression program, Immunity, Jul. 2002, pp. 51-62, vol. 17, No. 1.

Shapiro-Shelef, et al., Blimp-1 Is Required for the Formation of Immunoglobulin Secreting Plasma Cells and Pre-Plasma Memory B Cells, Immunity, Oct. 2003, pp. 607-620, vol. 19.

Shapiro-Shelef, et al., Blimp-1 is required for maintenance of long-lived plasma cells in the bone marrow, The Journal of Experimental Medicine, Dec. 5, 2005, pp. 1471-1476, vol. 202, No. 11.

Shen Chun-Pyn, et al., B-cell-specific DNA binding by an E47 homodimer, Molecular and Cellular Biology, 1995, pp. 4518-4524, vol. 15, No. 8.

Shvarts, et al., A senescence rescue screen identifies BCL6 as an inhibitor of anti-proliferative p19 ARF-p53 signaling, Genes and Development, Mar. 15, 2002, vol. 16, No. 6, pp. 681-686.

Solvason, et al., Transgene Expression of bcl-xL Permits Anti-immunoglobulin (Ig)-induced Proliferation in xid B Cells, J. Exp. Med., 1998, pp. 1081-1091, vol. 187.

Stier, et al., Notch1 activation increases hematopoietic stem cell self-renewal in vivo and favors lymphoid over myeloid lineage outcome, Blood, vol. 99, No. 7, Apr. 1, 2002, pp. 2369-2378, XP002317904, ISSN: 006-4971, p. 2375, left-hand column.

Tan, et al., Zinc-finger Protein-Targeted Gene Fegulation: Genomewide Single-Gene Specificitv, Proceedings of the National Academy of Sciences of the United States of America, Oct. 14, 2003, vol. 100, No. 21, pp. 11997-12002.

Tosato, et al., Identification of Interleukin-6 as an Autocrine Growth Factor for Epstein-Barr Virus-Immortalized B Cells, Journal of Virology, Jun. 1990, pp. 3033-3041, vol. 64, No. 6.

Toyama, et al., Memory B Cells Without Somatic Hypermutation Are Generated From Bcl6-Deficient B Cells, Immunity, Sep. 1, 2002, pp. 329-339, vol. 17, No. 3, Cell Press, US.

Traggiai, et al., Abstract; Development of a human adaptive immune system in cord blood cell-transplanted mice; Science (Washington, DC) vol. 304, No. 5667, Apr. 2, 2004, pp. 104-107, XP002356076, ISSN: 0036-8075, the whole document.

Traggiai, et al., Abstract; An efficient method to make human monoclonal antibodies from memory B cells: potent neutralization of SARS conoranavirus, Nature Medicine, Aug. 2004, pp. 871-875, vol. 10, No. 8.

Turner, et al., Blimp-1, a Novel Zinc Finger-Containing Protein That Can Drive the Maturation of B Lymphocytes into Immunoglobulin-Secreting Cells. Cell, Apr. 22, 1994, pp. 297-306, vol. 77.

Urlinger, et al., Exploring the sequence space for the tetracycline-dependent transcriptional activators: novel mutations yield expanded range and sensitivity, Proceedings of the National Academy of Sciences of USA, pp. 7963-7968, Jul. 5, 2000, vol. 97, No. 14, National Academy of Science, Washington, DC, US.

Van Regenmortel, Requirements for empirical immunogenicity trials, rather than structure-based design, for developing an effective HIV vaccine, Arch. Virol. (2012) 157: pp. 1-20.

Vickers, et al., Efficient reduction of target RNAs by small interfering RNA and RNase H-dependent antisense agents, 2003, The Journal of Biological Chemistry; vol. 278, pp. 7108-7118.

Weijer, et al., Intrathymic and extrathymic development of human plasmacytoid dendritic cell precursors in vivo; Blood, 2002; 99: 2752-2759.

Yamochi, et al. Adenovirus-mediated high expression of BCL-6 CV-1 cells induces apoptotic cell death accompanied by down-regulation of BCL-2 and BCL-XL, Oncogene, Jan. 14, 1999. pp. 487-494, vol. 18, No. 2.

Yang, et al. Generation of Functional antigen-specific T Cells in defined genetic backgrounds by retrovirus-mediated expression of TCR cDNAs in hematopoietic precursor cells, Proceedings of the National Academy of Sciences of USA, Apr. 30, 2002, pp. 6204-6209, vol. 99, No. 9, National Academy of Science, Washington, DC, US.

Zhang et al., Up-Regulation of Bcl-Xl Expression Protects CD40-Activated Human B Cells from Fas-Mediated Apoptosis, Cellular Immunology, 1996, pp. 149-154, vol. 173.

Zhou, et al., Improved single-chain transactivators of the Tet-On gene expression system, Biotechnology, 2007, p. 6, vol. 7.

Zhou, et al., Modification of the Tet-On regulatory system prevents the conditional-live HIV-1 variant from losing doxycycline-control, Retrovirology, 2006, p. 82, vol. 3.

Zhou, et al., Optimization of the Tet-On system for regulated gene expression through viral evolution, Gene Therapy, Oct. 2006, pp. 1382-1390, vol. 13, No. 39.

Zhou, et al., The genetic stability of a conditional live HIB-1 variant can be improved by mutations in the Tet-On regulatory system that restrain evolution, The Journal of Biological Chemistry, Jun. 23, 2006, pp. 17084-17091, vol. 281, No. 25.

Eaton, et al., Gene Therapy, 2002, vol. 9, pp. 527-535.

Kyba, et al., Enhanced hematopoietic differentiation of embryonic stem cells conditionally expressing Stat5. PNAS, 2003, vol. 100, pp. 1-12.

Manion, et al., Bcl-xL Mutations Suppress Cellular Sensitivity to Antimycin A, The Journal of Biological Chemistry, 2004, vol. 279, No. 3, pp. 2159-2165.

Petros, et al., Rationale for Bcl-xL/Bad Peptide Complex Formation From Structure, Mutagenesis, and Biophysical Studies, Protein Science, 2000, vol. 9, pp. 2528-2534, Cambridge University Press, USA.

Sayegh, et al., E-proteins directly regulate expression of activation-induced deaminase in mature B cells, nature immunology, vol. 4, No. 6, Jun. 2003, pp. 586-593.

Dimitrov, Jordan, et al., Thermodynamic stability contributes to immunoglobulin specificity, Trends in Biochemical Sciences, vol. 39, No. 5, May 1, 2014, pp. 221-226.

Klein, Florian, et al., Somatic Mutations of the Immunoglobulin Framework are Generally Required for Broad and Potent HIV-1 Neutralization, Cell, vol. 153, No. 1, Mar. 28, 2013, pp. 126-138.

Kwakkenbos, Mark, et al., Genetic manipulation of B cells for the isolation of rare therapeutic antibodies from the human repertoire, Methods, Academic Press, vol. 65, No. 1, Jan. 1, 2014, pp. 38-43.

McConnell, Audrey, et al., An intergrated approach to extreme thermostabilization and affinity maturation of an antibody, Protein Engineering Design and Protection, vol. 26, No. 2, Feb. 1, 2013, pp. 151-164.

Wang, Feng, et al., Somatic hypermutation maintains antibody thermodynamic stability during affinity maturation, Proceedings of the National Academy of Sciences, vol. 110, No. 11, Mar. 12, 2013, pp. 4261-4266.

(56) References Cited

OTHER PUBLICATIONS

Diehl, Sean A., et al.; "STAT3-Mediated Up-Regulation of BLIMP1 is Coordinated with BCL6 Down-Regulation to Control Human Plasma Cell Differentiation;" The Journal of Immunology, 2008, vol. 180, pp. 4805-4815.
Christopherson, Karen S., et al.; "Ecdysteroid-dependent regulation of genes in mammalian cells by a Drosophila ecdysone receptor and chimeric transactivators;" Proc. Natl. Acad. Sci. USA, Jul. 1992, vol. 89, pp. 6314-6318.
Chipuk, Jerry E., et al.; "How do BCL-2 proteins induce mitochondrial outer membrane permeabilization?;" Cell Press, Trends in Cell Biology; vol. 18, No. 4, pp. 157-164.
Banchereau, Jacques, et al.; "Long-Term Human B Cell Lines Dependent on Interleukin-4 and Antibody to CD40;" Sciences, Jan. 4, 1991, vol. 251, No. 4989, pp. 70-72.
Adams, Jerry M., et al.; "Bcl-2 regulated apoptosis: mechanism and therapeutic potential;" ScienceDirect, Current Opinion in Immunology; 2007, vol. 19, pp. 488-496.
Close, Pauline M., et al.; "Zonal Distribution of Immunoglobulin-Synthesizing Cells Within the Germinal Centre: An In Situ Hybridization and Immunohistochemical Study;" Journal of Pathology, 1990, vol. 162, pp. 209-216.
Liu, Yong-Jun, et al.; "Germinal center development;" Immunological Reviews, 1997, vol. 156, pp. 111-126.
Kinsella, Todd M., et al.; "Episomal Vectors Rapidly and Stably Produce High-Titer Recombinant Retrovirus;" Human Gene Therapy, Aug. 1, 1996, vol. 7; pp. 1405-1413.
Ye, Bihui H., et al.; "The BCL-6 proto-oncogene controls germinal-centre formation and Th2-type inflammation;" Nature Publishing Group, Jun. 16, 1997, vol. 16, pp. 161-170.
Zamore, Phillip D., et al.; "RNAi: Double-Stranded RNA Directs the ATP-Dependent Cleavage of mRNA at 21 to 23 Nucleotide Internals;" Cell, Mar. 31, 2000, vol. 101, pp. 25-33.
Ettinger, Rachel, et al.; "IL-21 Induces Differentiation of Human Naive and Memory B Cells into Antibody-Secreting Plasma Cells;" The Journal of Immunololgoy, 2005, vol. 175, pp. 7867-7879.
Johnson, Syd, et al.; "A Direct Comparison of the Activities of Two Humanized Respiratory Syncytial Virus Monoclonal Antibodies: MEDI-493 and RSHZ19;" The Journal of Infectious Disease, 1999, vol. 180, pp. 35-40.
Smit, Laura A., et al.; "Expression of Activation-induced Cytidine Deaminase is Confined to B-Cell Non-Hodgkin's Lymphomas of Germinal-Center Phenotype;" Cancer Research, Jul. 15, 2003, vol. 63, pp. 3894-3898.
Jung, Daniel, et al.; "Inducible Expression of Bcl-XL Restricts Apoptosis Resistance to the Antibody Secretion Phase in Hybridoma Cultures;" 2002 Wiley Periodicals Inc., pp. 180-187.
Liu, Xinqi, et al.; "The Structure of a Bcl-xL/Bim Fragment Complex: Implications for Bim Function;" Immunity, Sep. 2003, vol. 19, pp. 341-352.
Ning, Zhi-Qiang, et al.; "Distinct mechanisms for rescue from apoptosis in Ramos human B cells by signaling through CD40 and interleukin-4 receptor: role for inhibition of an early response gene;" Eur. J. Immunol., 1996, vol. 26, pp. 2356-2363.
Tey, Beng, et al.; "Effect of Bcl-2 Overexpression on Cell Cycle and Antibody Productivity in Chemostat Cultures of Myeloma NS0 Cells;" Journal of Bioscience and Bioengineering, 2005, vol. 100, No. 3, pp. 303-310.
Yoo, Esther M., et al.; "Myeloma expression systems;" Journal of Immunological Methods, 2002, vol. 261, pp. 1-20.
Baron, Udo, et al.; "Tet-Repressor-Based System for Regulated Gene Expression in Eukaryotic Cells: Principles and Advances;" Methods in Enzymology, vol. 327, pp. 401-421.
Guzman, Luz-Maria, et al.; "Tight Regulation, Modulation, and High-Level Expression by Vectors Containing the Arabinose PBAD Promoter;" Journal of Bacteriology, Jul. 1995, pp. 4121-4130.
Muramatsu, Masamichi, et al.; "Specific Expression of Activation-induced Cytidine Deaminase (AID), a Novel Member of the RNA-editing Deaminase Family in Germinal Center B Cells;" The Journal of Biological Chemistry, Jun. 25, 1999, vol. 274, No. 26, pp. 18470-18476.
Kee, Barbara L.; "E and ID proteins branch out;" Nature Reviews Immunology, Mar. 2009, vol. 9, pp. 175-184.
Kuo, Tracy C., et al.; "Repression of BCL-6 is required for the formation of human memory B cells in vitro;" The Journal of Experimental Medicine, Apr. 16, 2007, vol. 204, No. 4, pp. 819-830.
Lokate, Angelique M.C., et al.; "Biomolecular Interaction Monitoring of Autoantibodies by Scanning Surface Plasmon Resonance Microarray Imaging;" J. Am. Chem. Soc., 2007, vol. 129, pp. 14013-14018.
Malisan, Florence, et al.; "Interleukin-10 Induces Immunoglobulin G Isotype Switch Recombination in Human CD40-Activated Naive B Lymphocytes;" The Journal of Experimental Medicine, Mar. 1996, vol. 183, pp. 937-947.
Maurer, Ulrich, et al.; "Glycogen Synthase Kinase-3 Regulates Mitochondrial Outer Membrane Permeabilization and Apoptosis by Destabilization of MCL-1;" Molecular Cell, Mar. 17, 2006, vol. 21, pp. 749-760.
Ichikawa, H. Travis, et al.; "Structural Phylogenetic Analysis of Activation-Induced Deaminase Function;" The Journal of Immunology, 2006, vol. 177, pp. 355-361.
Peled, Jonathan U., et al.; "The Biochemistry of Somatic Hypermutation;" Annu. Rev. Immunol, 2008, vol. 26, pp. 481-511.
Gossen, Manfred, et al.; "Tight control of gene expression in mammalian cells by tetracycline-responsive promoters;" Proc. Natl. Acad. Sci. USA, Jun. 1992, vol. 89, pp. 5547-5551.
Rousset, Francoise, et al.; "Interleukin 10 is a potent growth and differentiation factor for activated human B lymphocytes;" Proc. Natl. Acad. Sci. USA, Mar. 1992, vol. 89, pp. 1890-1893.
Dadgostar, Hajir, et al.; "Cooperation of multiple signaling pathways in CD40-regulated gene expression in B lymphocytes;" PNAS, Feb. 5, 2002, vol. 99, No. 3, pp. 1497-1502.
Sidwell, Robert W., et al.; "Respiratory syncytial virus infections: Recent prospects for control;" ScienceDirect, Antiviral Research, 2006, vol. 71, pp. 379-390.
Spits, Hergen, et al.; "Id2 and Id3 Inhibit Development of CD34 Stem Cells into Predendritic Cell (Pre-DC)2 but Not into Pre-DC1: Evidence for a Lymphoid Origin of Pre-DC2;" J. Exp. Med., Dec. 18, 2000, vol. 192, No. 12, pp. 1775-1783.
Thompson, William W., et al.; "Mortality Associated With Influenza and Respiratory Syncytial Virus in the United States;" American Medical Association, Jan. 8, 2003, vol. 289, No. 2, pp. 179-186.
Hall, Caroline Breese, et al.; "The Burden of Respiratory Syncytial Virus Infection in Young Children;" The New England Journal of Medicine, Feb. 5, 2009, vol. 360, pp. 588-598.
Good, Kim L., et al.; "Kinetics of Human B Cell Behavior and Amplification of Proliferative Responses following Stimulation with IL-21;" The Journal of Immunology, 2006, vol. 177, pp. 5236-5247.
Ettinger, Rachel, et al.; "IL-21 is a Pivotal Cytokine in the Induction of TCell-Dependent B Cell Activation, Differentiation and IG Secretion;" Garn 2005 Novel Therapeutic Targets and Strategies, Section 107.
Ryvbal'skiy N.G., Serova M.A., Igant'yeva G.A., Starcheus A.P. "Monoklonal'nyye antitela gibribomy" (translation: Monoclonal antibodies and hybridomas), Moskva, Vaskhnil, 1989, pp. 23-44. English summary is attached.
Barnett, et al. Determination of leucocyte antibody binding capacity (ABC): the need for standardization. Clin. Lab. Haem., 1998, vol. 20, pp. 155-164.
Kwakkenbos, et al. Generation of Stable Monoclonal Antibody-Producing B Cell Receptor-Positive Human Memory B Cells by Genetic Programming. Nature Medicine, vol. 16, No. 1, Jan. 1, 2010, pp. 123-128.
Becker, et al. Generation of Human Antigen-Specific Monoclonal lgM Antibodies Using Vaccinated "Human Immune System" Mice, PLOS ONE, Oct. 4, 2010, vol. 5, No. 10.
Buckland, BLIMP1, BCL6, and B-Cell Fate, Nature Reviews Immunology, Sep. 2002, pp. 629-629, vol. 2.

(56) References Cited

OTHER PUBLICATIONS

Ozaki et al. Regulation of B Cell Differentiation and Plasma Cell Generation by IL-21, a Novel Inducer of Blimp-1 and Bcl-6, Journal of Immunology, American Association of Immunologists,US, Nov. 1, 2004, pp. 5361-5371, vol. 173, No. 9.
PCT International Search Report, PCT/EP2011/071676, dated Feb. 24, 2012.

* cited by examiner

A

■ B cells selected for high H3 binding
■ B cells selected for low H3 binding
■ B cells not selected (parental cells)

B

■ B cells selected for high H3 binding
■ B cells selected for low H3 binding
■ B cells not selected (parental cells)

Figure 7

| | Kappa light chain, CDR3 Position 108 | Kappa light chain, CDR1 Position 38 | Heavy chain, CDR1 Position 38 |
|---|---|---|---|
| Parental cells | AT10_004 | S | Y | G |
| Decreased affinity cells | AT10_004 mutant A | S | Y | A |
| Increased affinity cells | AT10_004 mutant B | Y | Y | G |
| Increased affinity cells | AT10_004 mutant C | Y | F | G |

MEANS AND METHODS FOR PRODUCING HIGH AFFINITY ANTIBODIES

CROSS-REFERENCE TO RELATED APPLICATIONS

This application is a continuation of and claims priority to U.S. application Ser. No. 13/990,988, filed Aug. 14, 2013, which claims priority to and the benefit of PCT/EP2011/071676 filed Dec. 2, 2011, which claims priority to and the benefit of U.S. Provisional Application 61/419,909 filed Dec. 6, 2010, which claims priority to and the benefit of European Patent Application Serial No. 10193562.5, filed Dec. 2, 2010, the entire contents of all of which are fully incorporated herein by reference.

SEQUENCE LISTING

This application incorporates by reference the Sequence Listing contained in an ASCII text file named "14956919.txt" submitted via EFS-Web. The text file was created on Dec. 22, 2017, and is 24 kb in size.

TECHNICAL FIELD

The invention relates to the field of cell biology. More specifically, it relates to the field of antibody production.

BACKGROUND

Ex vivo B-cell cultures are important tools in current biological and medical applications. One important application is culturing antibody-producing cells in order to harvest antibodies, preferably monoclonal antibodies. Monoclonal antibodies (mAbs) represent multiple identical copies of a single antibody molecule. Amongst the benefits of mAbs is their specificity for the same epitope on an antigen. This specificity confers certain clinical advantages on mAbs over more conventional treatments while offering patients an effective, well-tolerated therapy option with generally low side effects. Moreover, mAbs are useful for biological and medical research.

Mature B-cells can be cultured in vitro under conditions that mimic some key aspects of the germinal centre (GC) reaction; that is, activation of B-cells with CD40 ligand (L) and the presence of cytokines like interleukin (IL)-4, IL-10 or IL-21. While B-cells cultured with CD40L, IL-2 and IL-4 produce very little Ig, addition of IL-21 leads to differentiation to plasma cells accompanied by high 1 g secretion. Although this in vitro system has proven useful to study some aspects of B-cell differentiation, both naive IgD+ B-cells and switched IgD-memory B-cells eventually differentiate into terminally differentiated plasma cells, which is accompanied by cell cycle arrest precluding the generation of long-term antigen-specific BCR-positive cell lines.

Recent advances have provided insight into how multiple transcription factors, including B-lymphocyte-induced maturation protein 1 (BLIMP1) and B-cell lymphoma (BCL) 6 control development of GC B-cells into terminally arrested, antibody-producing plasma cells. The transcriptional repressor BCL6 has been shown to prevent plasma cell differentiation. BCL6 is highly expressed in GC B-cells where it facilitates expansion of B-cells by down-regulating p53 and prevents premature differentiation of GC cells into plasma cells by negatively regulating BLIMP1.

An improved method for generating an antibody-producing plasmablast-like B-cell was recently described in WO 2007/067046, which is hereby incorporated by reference. According to this method, the amount of BCL6 and a Bcl-2 family member, preferably Bcl-xL, are modulated in a B-cell, preferably a memory B-cell, to generate an antibody-producing plasmablast-like B-cell. In WO 2007/067046, the amount of BCL6 and/or Bcl-xL expression product is either directly or indirectly influenced. Preferably, the amounts of both BCL6 and Bcl-xL expression products within the antibody-producing cell are increased, since both expression products are involved in the stability of an antibody-producing B-cell. Bcl-xL is a member of the anti-apoptotic Bcl-2 family. Processes that are controlled by the Bcl-2 family, which includes both pro- and anti-apoptotic proteins, relate to the mitochondrial pathway of apoptosis. This pathway proceeds when molecules sequestered between the outer and inner mitochondrial membranes are released into the cytosol by mitochondrial outer membrane permeabilization. The pro-apoptotic family members can be divided in two classes. The effector molecules Bax and Bak, which contain so-called Bcl-2 homology domain 3 (BH3) domains, are involved in permeablilizing the outer mitochondrial membrane by forming proteolipid pores; the pro-apoptotic BH3-only proteins (Bad, Bik, Bim, Bid, Hrk, Bmf, bNIP3, Puma and Noxa) function upon different cellular stresses by protein-protein interactions with other (anti-apoptotic) Bcl-2 family members.

Anti-apoptotic Bcl-2 family members Bcl-2, Bcl-xL, Bcl-w, A1 and Mcl-1 are generally integrated with the outer mitochondrial membrane. They directly bind and inhibit the pro-apoptotic Bcl-2 proteins to protect mitochondrial membrane integrity.

In such a method, it is further preferred that the antibody-producing plasmablast-like B-cell is incubated with IL 21 and CD40L. A B-cell, such as an antibody-producing plasmablast-like B-cell, is preferably cultured in the presence of CD40L since replication of most B-cells is favored by CD40L. It is furthermore preferred that STAT3 is activated in the antibody-producing B-cell. Activation of STAT3 can be achieved in a variety of ways. Preferably, STAT3 is activated by providing an antibody-producing cell with a cytokine. Cytokines, being naturally involved in B-cell differentiation, are very effective in regulating STAT proteins. Very effective activators of STAT3 are IL-2, IL-10, IL-21 and IL-6, but also IL-7, IL-9, IL-15, IL-23 and IL-27 are known to activate STAT3. Additionally, or alternatively, STAT3 activation is accomplished by transfer into a B-cell of a nucleic acid encoding a mutant of STAT3 that confers constitutive activation to STAT3. (Sean A. Diehl, Heike Schmidlin, Maho Nagasawa, Simon D. van Haren, Mark J. Kwakkenbos, Etsuko Yasuda, Tim Beaumont, Ferenc A. Scheeren, Hergen Spits STAT3-mediated up-regulation of BLIMP1 is coordinated with BCL6 down-regulation to control human plasma cell differentiation. J. Immunol. 2008 vol. 180 (7) pp. 4805-15.)

Most preferably, IL-21 is used, since IL-21 is particularly suitable for influencing the stability of an antibody producing plasmablast-like B-cell. In addition to up-regulating STAT3, IL-21 is capable of up-regulating BLIMP1 expression even when BLIMP1 expression is counteracted by BCL6. With the methods disclosed in WO 2007/067046, it has become possible to increase the replicative life span of an antibody-producing cell since it is possible to maintain a B-cell in a developmental stage wherein replication occurs. In earlier ex vivo B-cell cultures, the replicative life span was only a few weeks to two months. During this time, the cultured cells lose their capability of replicating and die. With a method as disclosed in WO 2007/067046, however, it has become possible to prolong the replicative life span of antibody-producing memory B-cells, so that ex vivo cultures are generated comprising plasmablast-like B-cells that are capable of replicating and producing antibody.

Although these methods enable the production of antibodies that efficiently target an antigen of interest, improvement of antibody characteristics, such as binding affinity, is often desired. Binding characteristics are, therefore, regularly altered by introducing mutations in the encoding nucleic acid, preferably in the CDR encoding region, and testing the resulting antibodies. This is, however, time consuming. Alternative methods for obtaining high affinity antibodies are, therefore, desired.

It is an object of the present invention to provide methods for producing and/or selecting high affinity antibodies.

The invention provides means and method for obtaining a B-cell population, starting from a given B-cell culture, which population has a higher average binding capacity than the original B-cell culture. Preferably, a monoclonal B-cell population is produced, starting from a monoclonal B-cell culture. Provided is a simple and elegant way of obtaining B-cell populations with an increased average binding capacity, without the need for laborious mutation techniques.

The invention provides a method for producing antibodies specific for an antigen of interest comprising:
 a) selecting a B-cell capable of producing antibody specific for the antigen of interest or selecting a B-cell capable of differentiating into a B-cell that is capable of producing antibody specific for the antigen of interest;
 b) inducing, enhancing and/or maintaining expression of BCL6 in the B-cell;
 c) inducing, enhancing and/or maintaining expression of an anti-apoptotic nucleic acid in the B-cell;
 d) allowing expansion of the B-cell into a population of the B-cells;
 e) selecting at least one B-cell from the population of B-cells producing a B-cell receptor and/or antibody with a binding capacity higher than the average binding capacity of the population of B-cells for the antigen of interest;
 f) culturing the at least one B-cell into a population of B-cells; and
 g) obtaining antibodies produced by the B-cell culture.

Within a population of monoclonal B-cells capable of producing antibody specific for an antigen of interest, it is possible to select, in step e) of a method hereof, at least one, optionally more than one, such as, for instance, 2, 3, 4, 5, 6, 7, 8, 9, 10, 20, 25 or 50 B-cells with a binding capacity for the antigen of interest that is higher than the average binding capacity of the population of B-cells for the antigen of interest. Such B-cells with a higher binding capacity for an antigen of interest than the average binding capacity of the population of B-cells for the antigen of interest are herein also called "high-affinity B-cells." One possible reason for a difference in binding capacity between multiple B-cells in a monoclonal population of B-cells is that the expression of the BCR varies between B-cells in the population. A B-cell with a relatively high expression of the BCR will bind more antigen of interest than a B-cell with a relatively low expression of the BCR. However, it is expected that antibodies produced by B-cells with different expression of the BCR have the same binding affinity. The present inventors surprisingly found that, besides a relatively high BCR expression, a collection of high-affinity B-cells produce antibodies specific for the antigen of interest that bind the antigen with a higher affinity than the average affinity of antibodies produced by the population of B-cells. Even more surprisingly, the inventors found that the B-cell cultures obtained with a method hereof contained cells that bound antigen with a higher affinity than the average B-cell in the original culture. Single B-cells can thus be isolated from a given B-cell population on the basis of their higher binding capacity by methods known in the art and be expanded to a new B-cell population in at least three weeks. These new B-cells produce antibodies that have a higher affinity than the antibodies produced by the original B-cell population that the new B-cells are derived from. This finding is contrary to expectations because a person skilled in the art would expect that after isolation of one B-cell (subclone) from an already monoclonal population of B-cells, the affinity for the antigen of antibody produced by the progeny of the subclone of the already monoclonal B-cell population will return to the average affinity for the antigen, comparable to the average affinity of the population of B-cells from which the at least one B-cell was selected.

Thus, in one embodiment in step a) of a method hereof, preferably a single B-cell is selected, for instance, from a polyclonal population of B-cells. The single B-cell is subsequently expanded into a monoclonal population of B-cells in steps b) to d). This is, for instance, achieved using a method as described in WO 2007/067046, which is discussed hereinbefore. Hence, in step d), a monoclonal B-cell line specific for an antigen of interest is obtained. In principle, all B-cells in the monoclonal B-cell line produce essentially the same antibodies specific for the antigen, although small differences in the affinity for the antigen may be present between cells of the monoclonal B-cell line, i.e., some B-cells in the monoclonal population produce antibodies with an affinity that is slightly higher than the average affinity and some B-cells in the monoclonal population produce antibodies with a slightly lower affinity. The population of B-cells becomes slightly heterogeneous again. In step e), at least one of such B-cells with a higher affinity than the average affinity is selected from the monoclonal B-cell line. In step f), the B-cell or B-cells selected in step e) are subsequently cultured into a second, preferably monoclonal, B-cell line. Provided is the insight that this second, preferably monoclonal, B-cell line has an average affinity that is higher than the average affinity of the original monoclonal B-cell population obtained in step d). As described above, it was surprisingly found that the high affinity of a selected B-cell is maintained after culturing, even if culturing takes place during a prolonged period of time, instead of returning to the average affinity of the original population. Thus, the second monoclonal population of B-cells cultured in step f) has a higher average affinity for the antigen than the monoclonal population of B-cells cultured in step d). Similarly, the affinity of most B-cells in the second monoclonal population of step f) is higher than the affinity of most B-cells in a monoclonal population of step d).

The invention thus provided in one embodiment is a method for obtaining a B-cell population with an increased average affinity for an antigen of interest, as compared to an original monoclonal B-cell population with a given average affinity for the antigen of interest, the method comprising:
 providing a monoclonal B-cell population that is specific for the antigen of interest,
 selecting at least one B-cell from the population of B-cells producing a B-cell receptor and/or antibody with a binding capacity higher than the average binding capacity of the population of B-cells for the antigen of interest; and
 culturing the at least one B-cell into a population of B-cells.

Further provided is a method for producing antibodies specific for an antigen of interest, the method comprising:

a) selecting a single B-cell capable of producing antibody specific for the antigen of interest or selecting a B-cell capable of differentiating into a B-cell that is capable of producing antibody specific for the antigen of interest;

b) inducing, enhancing and/or maintaining expression of BCL6 in the B-cell;

c) inducing, enhancing and/or maintaining expression of an anti-apoptotic nucleic acid in the B-cell;

d) allowing expansion of the B-cell into a first monoclonal B-cell line;

e) selecting from the first monoclonal B-cell line at least one B-cell that produces a B-cell receptor and/or antibody with a binding capacity for the antigen of interest higher than the average binding capacity of the first monoclonal B-cell line;

f) culturing the at least one B-cell selected in step e) into a second, preferably monoclonal, B-cell line; and g) obtaining antibodies produced by the second, preferably monoclonal, B-cell line. Antibodies are obtained that have an affinity for the antigen of interest that is higher than the average affinity for the antigen of interest of antibodies produced by B-cells of the first monoclonal B-cell line.

In another embodiment, more than one B-cell is selected in step a) of a method hereof; for instance, 2, 3, 4, 5, 10, 15, 25, 50 or 100 B-cells. The B-cells are, for instance, selected from a polyclonal population of B-cells or from a biological sample. The selected B-cells are subsequently expanded into a population of B-cells in steps b) to d), for instance, using a method as described in WO 2007/067046. The obtained B-cell population is thus a (second) polyclonal B-cell population. Thereafter, and before step e) of a method hereof is carried out, a monoclonal population of B-cells is preferably produced. This is, for instance, done by selecting a single B-cell from the (second) polyclonal population of B-cells using Fluorescence Activated Cell Sorting or limiting dilution, which are explained hereinbelow, and expanding the selected single B-cell to a monoclonal population of B-cells. Then, step e) of a method hereof is carried out, in which at least one B-cell with a higher affinity than the average affinity of the monoclonal B-cell population is selected. In step f), the B-cell or B-cells selected in step e) are subsequently cultured into a second monoclonal B-cell line, after which, antibodies produced by the second monoclonal B-cell line are obtained in step g).

A method as described herein allows for obtaining improved, high-affinity antibodies, preferably monoclonal antibodies, without the use of recombinant techniques. Before the instant disclosure, affinity of (monoclonal) antibodies is increased using such recombinant techniques. The sequence of the nucleic acid encoding the antibody first needs to be determined. Subsequently, one or more mutations are introduced into the sequence of the nucleic acid encoding the antibody. Then, the genes containing one or more mutations need to be expressed in a cell followed by production of antibodies in producer cells. Finally, the mutated antibody has to be tested for its binding capacity to the antigen of interest in order to determine whether antibody with an improved affinity for the antigen as compared with the non-mutated antibody is obtained. Such a process for improving the affinity of an antibody is elaborate and time consuming. A method according to the instant disclosure allows the production of high-affinity antibody in a straight-forward and less elaborate process without the need of molecular engineering.

In one embodiment hereof, after the step of selecting at least one high-affinity B-cell from the already monoclonal population of B-cells (step e) of a method hereof as described above), the at least one high-affinity B-cell is allowed to expand into a population of B-cells, preferably a monoclonal B-cell line, again, after which another step of selecting at least one high-affinity B-cell from the new population of B-cells, preferably from the new monoclonal B-cell line, is performed. By repeating the steps of allowing expansion of a selected B-cell into a population and selecting at least one B-cell on the basis of its binding capacity for an antigen, i.e., repeating steps d) and e), it is possible to generate high-affinity antibody-producing B-cells. Preferably, by repeating the steps of expansion and selection as described above, it is possible to increase with each selection cycle the affinity of antibody produced by the resulting B-cell population for the antigen of interest.

A method is thus provided comprising, following step e) of a method hereof, repeating the step of allowing expansion of at least one selected high-affinity B-cell into a population of B-cells, preferably a monoclonal B-cell line, and selecting again at least one high-affinity B-cell, i.e., repeating steps d) and e) of a method hereof at least once. The steps are, for instance, repeated once, but preferably twice, three times, four times, five times or even more times.

In one embodiment, a method hereof is provided wherein the at least one B-cell selected in step e) is cultured for at least four weeks. Preferably, the at least one B-cell selected in step e) is cultured for at least six weeks, more preferably for at least nine weeks, more preferably for at least three months, more preferably for at least six months.

Without being bound to any theory, it is believed that differences in the affinity of antibodies for an antigen of interest within a population of monoclonal B-cells may result from processes mediated by Activation Induced Cytidine Deaminase (AID). Antigen-activated naive and memory B-cells in the germinal centre undergo extensive proliferation, accompanied by somatic hypermutations (SHM) and class-switch recombination (CSR) of 1 g genes mediated by AID. AID deaminates deoxycytidine residues in immunoglobulin genes, which triggers antibody diversification. It was demonstrated in patent application US2008305076 that IL 21 induces BLIMP, BCL6 and AID expression, but does not directly induce somatic hypermutation. However, the present inventors found that AID is expressed in B-cells that are cultured according to a method as herein described. The expression of AID in (a B-cell that will develop into) an antibody-producing B-cell allows the generation of novel immunoglobulins that harbor mutations that were not present in the original B-cell before transduction with BCL6 and an anti-apoptotic nucleic acid. Thus, culturing B-cells in which somatic hyper mutation is induced by expression of AID allows the generation of immunoglobulin variants that, for example, have a higher or lower affinity for an antigen of interest, or that are more stable, for example, in an aqueous solution or under increased salt conditions, or any combination thereof.

Upon selection of at least one high-affinity B-cell from the population of B-cells, AID is still expressed within the selected at least one B-cell. Therefore, after selection of such a B-cell, AID in the B-cell still allows the introduction of mutations in the immunoglobulin gene of the progeny of the B-cell. Somatic hypermutations in immunoglobulin genes occur preferentially in the CDR3 region of the Ig genes. Mutations introduced in the CDR3 region of the immunoglobulin are more likely to result in a reduced or lost binding affinity for an antigen of the immunoglobulin than in an increased binding affinity. The present inventors, however, did find increased binding affinity.

As used herein, the term "anti-apoptotic nucleic acid" refers to a nucleic acid that is capable of delaying and/or preventing apoptosis in a B-cell. Preferably, the anti-apoptotic nucleic acid is capable of delaying and/or preventing apoptosis in an antibody-producing B-cell. Preferably, an anti-apoptotic nucleic acid is used that comprises an exogenous nucleic acid. This means that either a nucleic acid sequence is used that is not naturally expressed in B-cells, or that an additional copy of a naturally occurring nucleic acid is used, so that expression in the resulting B-cells is enhanced as compared to natural B-cells. Various anti-apoptotic nucleic acids are known in the art, so that various embodiments are available. Preferably, a gene encoding an anti-apoptotic molecule is used. More preferably, a nucleic acid is used that is an anti-apoptotic member of the Bcl-2 family because anti-apoptotic Bcl-2 proteins are good apoptosis inhibitors. Many processes that are controlled by the Bcl-2 family (which family includes both pro- and antiapoptotic proteins) relate to the mitochondrial pathway of apoptosis, as outlined in more detail hereinbelow. Anti-apoptotic Bcl-2 family members Bcl-2, Bcl-xL, Bcl-w, A1 and Mcl-1 are preferred because they are generally integrated with the outer mitochondrial membrane. They directly bind and inhibit the pro-apoptotic proteins that belong to the Bcl-2 family to protect mitochondrial membrane integrity.

In a particularly preferred embodiment, the anti-apoptotic polynucleotide encodes Bcl-xL and/or Mcl-1 and/or a functional part of Bcl-xL and/or a functional part of Mcl-1. A combination of BCL6 and Bcl-xL nucleic acids, as well as a combination of BCL6 and Mcl-1 nucleic acids, is particularly suitable for immortalizing B-cells and long-term culture of the resulting plasmablast-like B-cells. Most preferably, the anti-apoptotic nucleic acid encodes Bcl-xL or a functional part thereof, because a combination of BCL6 and Bcl-xL stabilizes B-cells particularly well.

A functional part of Bcl-xL and a functional part of Mcl-1 are defined herein as fragments of Bcl-xL and Mcl-1, respectively, that have retained the same kind of anti-apoptotic characteristics as full-length Bcl-xL and Mcl-1, respectively, in kind (but not necessarily in amount). Functional fragments of Bcl-xL and Mcl-1 are typically shorter fragments of Bcl-xL and Mcl-1, which are capable of delaying and/or preventing apoptosis in a B-cell. Such functional fragments are, for instance, devoid of sequences that do not contribute to the anti-apoptotic activity of Bcl-xL or Mcl-1.

A population of B-cells hereof preferably is a monoclonal population of B-cells. An example of a population of B-cells hereof is a cell line of B-cells, preferably monoclonal B-cells. Hence, a population of B-cells hereof is most preferably a monoclonal B-cell line. Allowing expansion of the B-cell into a population of the B-cells is, for instance, accomplished by culturing the B-cell until a population of the B-cells is obtained.

Within a population of B-cells, even in a population of monoclonal B-cells, the binding capacity of the BCRs of the B-cells of the population, and the binding capacity of the antibodies produced by the B-cells of the population, is not equal. Instead, variation in the binding capacity exists. The average binding capacity of a population of B-cells is herein defined as the average of the binding capacity or average affinity of the BCR and/or antibody of all individual B-cells in the population. The average affinity for an antigen of interest of an antibody produced by a B-cell or by a population of B-cells is herein defined as the average of the affinities for the antigen of interest of the antibodies produced by all individual B-cells in the population. A high-affinity B-cell from a population of B-cells hereof, preferably from a monoclonal B-cell line, is preferably selected from the upper 40% of the B-cells of a population, preferably of a monoclonal B-cell line, with respect to binding capacity and/or affinity, preferably from the upper 30% of the B-cells of the population or monoclonal B-cell line, more preferably from the upper 25% of the B-cells of the population or monoclonal B-cell line, more preferably from the upper 20% of the B-cells of the population or monoclonal B-cell line, more preferably from the upper 15% of the B-cells of the population or monoclonal B-cell line, more preferably from the upper 10% of the B-cells of the population or monoclonal B-cell line, more preferably from the upper 1% of the B-cells of the population or monoclonal B-cell line. In one embodiment, one high-affinity B-cell is selected from the upper 1% of the B-cells of a population or monoclonal B-cell line with respect to binding capacity and/or affinity.

The average affinity for an antigen of interest of antibody produced by a population of B-cells, preferably by a monoclonal B-cell line, cultured from at least one high-affinity B-cell hereof is preferably at least 1.1 times the average affinity for the antigen of interest of the population of B-cells from which the at least one high-affinity B-cell was selected, more preferably at least 1.2, 1.3, 1.4, 1.5, 1.6, 1.7, 1.8, 1.9, 2.0, 2.1, 2.2, 2.3, 2.4, 2.5, 3.0, 3.5, 4.0, 5.0, 10.0, 20, 50, 100 times, or more, the average affinity for the antigen of interest.

The affinity of an antibody can be determined using any method known to a person skilled in the art. The affinity of an antibody is, for instance, determined using Enzyme-linked immunosorbent assay (ELISA), Surface Plasmon Resonance (such as Biacore) or Octet (ForteBio). Surface Plasmon Resonance (SPR) and Octet are techniques to measure biomolecular interactions in real-time in a label-free environment. For SPR, one of the interactants, for instance, an antibody, is immobilized to the sensor surface, the other, for instance, antigen, is free in solution and passed over the surface. Association and dissociation is measured in arbitrary units and preferably displayed in a sensorgram. Any change in the number of molecules bound to the biosensor tip causes a shift in the interference pattern that can be measured in real-time. Using Octet, the interference pattern of white light reflected from two surfaces, a layer of immobilized protein on the biosensor tip, and an internal reference layer is analyzed. The binding between a ligand immobilized on the biosensor tip surface, for instance, an antibody, and a protein in solution, for instance, an antigen of interest, produces an increase in optical thickness at the biosensor tip, which results in a wavelength shift that is a direct measure of the change in thickness of the biological layer. ELISA comprises immobilizing a protein, for instance, the antigen of interest, on the surface of the solid support, for example, a 96-well plate, and applying a sample to be detected or quantified on the solid support. Alternatively, a capture antibody is fixated on the surface of a solid support after which a sample containing the protein to be detected or quantified is applied to the immobilized capture antibody allowing the protein of interest to bind. Non-binding proteins are then washed away. Subsequently, a specific antibody conjugated to a label or an enzyme (or a primary antibody followed by a secondary antibody conjugated to a label or an enzyme) is added to the solid support. Preferably, the affinity constant ($K_D$) of an antibody produced by a B-cell hereof is determined.

Binding of a B-cell hereof to an antigen of interest can be measured using any method known to a person skilled in the art. For instance, an antigen of interest is labeled with, for example, a fluorescent label. Detection of binding can subsequently be determined by various techniques, among which fluoresce microscopy and Fluorescence Activated Cell Sorting (FACS). FACS allows separation of cells in a suspension on the basis of size and the fluorescence of conjugated antibodies directed against surface antigens.

Selecting at least one high-affinity B-cell from a population of B-cells, preferably from a monoclonal B-cell line, can be performed using any method known to a person skilled in the art. Selection of at least one high-affinity B-cell hereof is, for instance, performed by cell sorting, for instance, using FACS (see above) or limited dilution. Limited dilution comprises the serial dilution of a suspension of cells, for instance, B-cells, until a single cell is present in a given volume. Subsequently, the binding capacity of each B-cell (after expansion of single cells to a population) is tested to allow selection of a B-cell-producing antibodies with a high affinity for antigen.

A B-cell capable of producing antibody is defined as a B-cell that is capable of producing and/or secreting antibody or a functional part thereof, and/or that is capable of developing into a cell that is capable of producing and/or secreting antibody or a functional part thereof.

A functional part of an antibody is defined as a part that has at least one same property as the antibody in kind, not necessarily in amount. The functional part is preferably capable of binding a same antigen as the antibody, albeit not necessarily to the same extent. A functional part of an antibody preferably comprises a single domain antibody, a single chain antibody, a FAB fragment, a nanobody, a unibody, a single chain variable fragment (scFv), or a F(ab')$_2$ fragment.

Non-limiting examples of a B-cell used or selected in a method hereof include B-cells derived from a human individual, rodent, rabbit, llama, pig, cow, goat, horse, ape, chimpanzee, macaque and gorilla. Preferably, the B-cell is a human cell, a murine cell, a rabbit cell, an ape cell, a chimpanzee cell, a macaque cell and/or a llama cell. Most preferably, the B-cell is a human B-cell.

In a preferred embodiment, a memory B-cell is selected in step a) of the method as described herein, for instance, a human memory B-cell. In a particularly preferred embodiment, the memory B-cell is a peripheral blood memory B-cell. Peripheral blood memory B-cells are easily obtained, without much discomfort for the individual from which they are derived, and appear to be very suitable for use in a method according to the instant disclosure.

A B-cell or a population of B-cells, preferably a monoclonal B-cell line, obtained with a method hereof is preferably stable for at least four weeks, more preferably at least six weeks, more preferably at least nine weeks, more preferably for at least three months, more preferably for at least six months, meaning that such B-cells are capable of both replicating and producing antibody, or capable of replicating and developing into a cell that produces antibody, during the time periods. B-cells hereof preferably comprise cells producing IgM or cells producing other immunoglobulin isotypes like IgG, or IgA, or IgE, preferably IgG. A B-cell hereof is particularly suitable for use in producing an antibody-producing cell line. High-affinity B-cells or a population or monoclonal B-cell line of high affinity B-cells hereof are preferably cultured ex vivo and antibody is preferably collected for further use. Antibodies or functional parts thereof produced with a method hereof are useful for a wide variety of applications, such as, for instance, therapeutic, prophylactic and diagnostic applications, as well as research purposes and ex vivo experiments. For instance, a screening assay is performed wherein antibodies or functional parts hereof are incubated with a sample in order to determine whether an antigen of interest is present.

In one embodiment, a high-affinity B-cell or a population or monoclonal B-cell line of high-affinity B-cells hereof comprises a human B-cell, capable of producing human antibody, because human antibodies are particularly suitable for therapeutic and/or prophylactic applications in human individuals.

The expression of BCL6 in a B-cell is induced, enhanced and/or maintained in a variety of ways. In one embodiment, a B-cell is provided with a nucleic acid encoding BCL6 or a homologue. In another embodiment, a B-cell is provided with a compound capable of directly or indirectly enhancing BCL6 expression. Such compound preferably comprises a Signal Transducer of Activation and Transcription 5 (STAT5) protein or a functional part, derivative and/or analogue thereof, and/or a nucleic acid sequence coding therefor. STAT5 is a signal transducer capable of enhancing BCL6 expression. There are two known forms of STAT5, STAT5a and STAT5b that are encoded by two different, tandemly linked genes. Administration and/or activation of STAT5 results in enhanced BCL6 levels. Hence, down-regulation of BCL6 by BLIMP1 is at least in part compensated by up-regulation of expression of BCL6 by STAT5 or a functional part, derivative and/or analogue thereof. Hence, STAT5 or a functional part, derivative and/or analogue thereof is capable of directly influencing BCL6 expression. It is also possible to indirectly influence BCL6 expression. This is, for instance, done by regulating the amount of a compound that, in turn, is capable of directly or indirectly activating STAT5 and/or regulating STAT5 expression. Hence, in one embodiment, the expression and/or activity of endogenous and/or exogenous STAT5 is increased. It is, for instance, possible to indirectly enhance BCL6 expression by culturing an antibody-producing cell in the presence of interleukin (IL) 2 and/or IL 4 or other cytokines that are capable of activating STAT5.

It is furthermore preferred that in a method hereof, the B-cells are at least at some stage incubated with IL 21 and CD40L. A B-cell, such as an antibody-producing plasmablast-like B-cell, is preferably cultured in the presence of CD40L since replication of most B-cells is favored by CD40L. It is furthermore preferred that STAT3 is activated in the B-cell. Most preferably, IL 21 is used for up-regulating STAT3, since IL 21 is particularly suitable for influencing the stability of a B-cell hereof. In addition to up-regulating STAT3, IL 21 is capable of up-regulating BLIMP1 expression even when BLIMP1 expression is counteracted by BCL6.

In another embodiment, the amount of BLIMP1 expression product in the B-cell selected in step a) of a method hereof is directly or indirectly controlled. The amount of BLIMP1 expression product can be controlled in various ways, for instance, by regulating STAT3 or a functional part, derivative or analogue thereof STAT3 is activated in a variety of ways. Preferably, STAT3 is activated by providing a B-cell hereof with a cytokine. Cytokines, being naturally involved in B-cell differentiation, are very effective in regulating STAT proteins. Very effective activators of STAT3 are IL-21 and IL-6, but also IL-2, IL-7, IL-10, IL-15 and IL-27 are known to activate STAT3. Moreover, Toll-like receptors (TLRs) that are involved in innate immunity are also capable of activating STAT3. Most preferably, IL-21 is used. IL-21 is capable of up-regulating BLIMP1 expression even when BLIMP1 expression is counteracted by BCL6.

By "a functional part of STAT5 or STAT3" is meant a proteinaceous molecule that has the same capability—in kind, not necessarily in amount—of influencing the stability of an antibody-producing cell as compared to STAT5 or STAT3, respectively. A functional part of a STAT5 protein or a STAT3 protein is, for instance, devoid of amino acids that are not, or only very little, involved in said capability. A derivative of STAT5 or STAT3 is defined as a protein that has been altered such that the capability of the protein of influencing the stability of an antibody-producing cell is essentially the same in kind, not necessarily in amount. A derivative is provided in many ways, for instance, through conservative amino acid substitution wherein one amino acid is substituted by another amino acid with generally similar properties (size, hydrophobicity, etc.), such that the overall functioning is likely not to be seriously affected. A derivative, for instance, comprises a fusion protein, such as a STAT5-ER fusion protein whose activity depends on the presence of 4 hydroxy-tamoxifen (4HT). An analogue of STAT5 or STAT3 is defined as a molecule having the same capability of influencing the stability of an antibody-producing cell in kind, not necessarily in amount. The analogue is not necessarily derived from the STAT5 or STAT3 protein.

A method hereof is preferably used for generating a cell line of high-affinity B-cells that is stable for at least one week, preferably at least one month, more preferably at least three months, more preferably at least six months so that commercial high-affinity antibody production has become possible. Preferably, a stable cell line capable of producing monoclonal high-affinity antibodies is produced. This is preferably performed by using memory B-cells that have, for instance, been isolated from a sample by selection for CD19 (B-cell marker) and cell surface IgG and/or CD27 (to mark memory cells). Furthermore, a memory B-cell capable of specifically binding an antigen of interest is, for instance, selected in a binding assay using the antigen of interest. Subsequently, BCL6 and an anti-apoptotic nucleic acid, preferably Bcl-XL or Mcl-1, are preferably co-expressed in the B-cell, resulting in a population of cells specific for the antigen of interest. Preferably, only one memory cell is selected in step a) of a method as described herein, so that a B-cell population hereof producing monoclonal antibodies (a monoclonal B-cell line) is obtained.

In one embodiment, a B-cell, preferably, but not necessarily, a memory B-cell, that originates from an individual that had been previously exposed to an antigen of interest, is used in a method hereof. However, this is not necessary. It is also possible to use a B-cell from an individual that has not been exposed to the antigen of interest. For instance, a B-cell is used that is specific for another antigen but shows cross-reactivity with the antigen of interest. As another example, a B-cell is used that is selected from a naive B-cell population of an individual. The naive B-cell population of an individual may contain B-cells that show reactivity with an antigen of interest even though the individual has not been exposed to the antigen of interest. Such B-cell from a naive B-cell population is, for instance, selected using labeled antigen of interest.

The invention furthermore provided are isolated or recombinant B-cells and populations of B-cells, preferably monoclonal B-cell lines, obtained by a method hereof. Such high-affinity B-cells are preferably stable for at least one week, preferably for at least one month, more preferably for at least three months, more preferably for at least six months, meaning that the B-cell is capable of both replicating and producing antibody, or capable of replicating and developing into a cell that produces antibody, during the time periods. B-cells hereof preferably comprise cells producing IgM or cells producing other immunoglobulin isotypes like IgG, or IgA, or IgE, preferably IgG. A B-cell hereof is particularly suitable for use in producing an antibody-producing cell line. High-affinity B-cells hereof are preferably cultured ex vivo and antibody is preferably collected for further use. Antibodies obtained from a B-cell or from a B-cell population or monoclonal cell line hereof are also provided. High-affinity antibodies or functional parts thereof produced with a method hereof are useful for a wide variety of applications, such as, for instance, therapeutic, prophylactic and diagnostic applications, as well as research purposes and ex vivo experiments. For instance, a screening assay is performed wherein antibodies or functional parts hereof are incubated with a sample in order to determine whether an antigen of interest is present.

B-cells generated with a method hereof are particularly suitable for producing high-affinity antibodies against an antigen of interest. In one preferred embodiment, however, the genes encoding the Ig heavy and/or light chains are isolated from the cell and expressed in a second cell, such as, for instance, cells of a Chinese hamster ovary (CHO) cell line. The second cell, also called herein a "producer cell," is preferably adapted to commercial antibody production. Proliferation of the producer cell results in a producer cell line capable of producing antibody. Preferably, the producer cell line is suitable for producing compounds for use in humans. Hence, the producer cell line is preferably free of pathogenic agents such as pathogenic micro-organisms.

The invention is further explained by the following, non-limiting, examples.

BRIEF DESCRIPTION OF THE DRAWINGS

FIG. 7. Overview of the amino acid changes that were found in the selected subpopulations with increased or decreased affinity. Mutations in the sequence of AT10_004 that were associated with increased H3 antigen binding were incorporated in the AT10_004 sequence and these antibodies were produced recombinant in 239T cells and purified for further analysis (AT10_004 mutant B and AT10_004 mutant C).

EXAMPLES

Example 1

Figure 1:
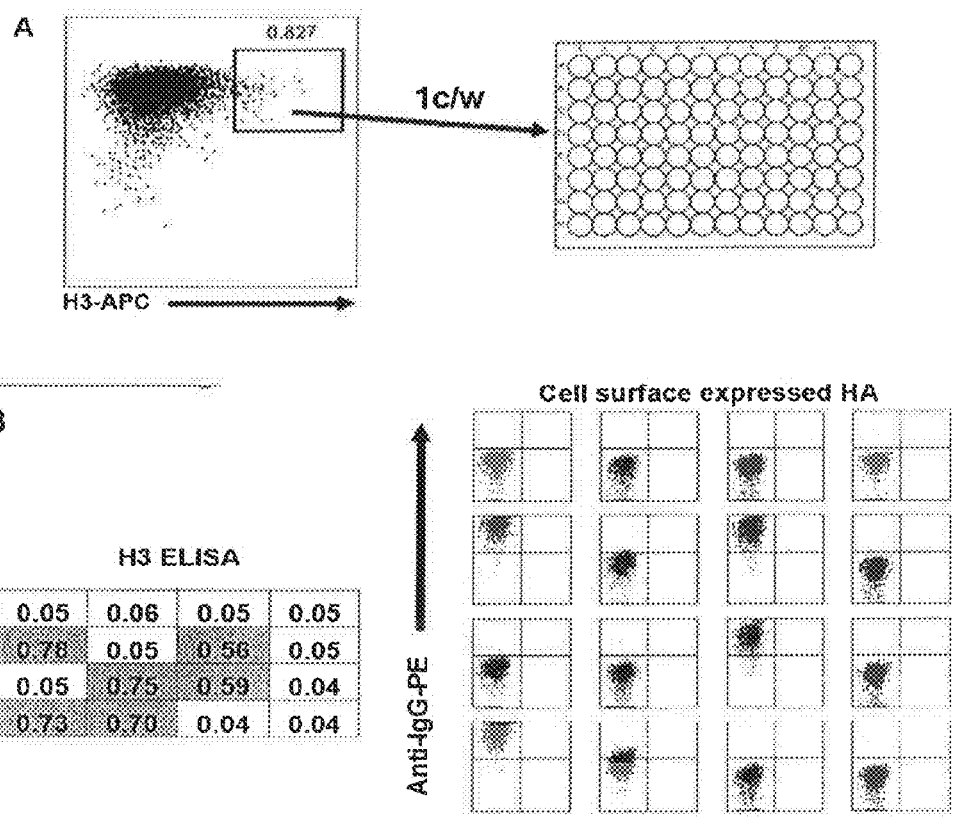
FIG. 1. Panel A: Binding of labeled HA H3 protein to the BCR of H3-specific cells within a polyclonal B-cell population. B-cells that bind the H3 protein with high affinity were cloned by single cell sorting. After two to three weeks of culture, the culture supernatant was screened for H3-specific antibodies. Panel B: Example of the screening performed to select H3-specific clones. Panel B (Left): Screening by ELISA. Recombinant H3 protein was coated onto a plate followed by incubation with culture supernatant. Antibody binding was detected using anti-human-IgG-HRP. Panel B (Right): Screening on cell surface-expressed HA. H3N2-infected cells were incubated with B-cell culture supernatant. Antibody binding was detected with a PE-labeled goat anti-human F(ab') 2.

Generation of an Anti-Influenza Hemaglutinin (HA) H3-Specific Monoclonal Human Antibody Human memory B-cells were immortalized using the BCL6/Bcl-xL technology described by Kwakkenbos et al. (Generation of stable monoclonal antibody-producing B-cell receptor-positive human memory B-cells by genetic programming, Nature Medicine (2010) vol. 16 (1) pp. 123-8, and patent application MEANS AND METHODS FOR INFLUENCING THE STABILITY OF ANTIBODY PRODUCING CELLS [WO 2007/067046]). In brief, BCL6 and Bcl-xL-transduced cells (GFP-positive) were cultured with CD40Ligand-expressing L-cells and interleukin (IL)-21 before the HA H3 binding cells were sorted using the Fluorescence activated cell sorter (FACS) (FIG. 1, Panel A). The Influenza HA protein (Protein Sciences) was labeled with Alexa Fluor 647 (Molecular Probes) and incubated with polyclonal cultured B-cells. HA-positive cells were sorted single cell per well and maintained in culture for two to three weeks before the clones were screened for HA binding by 1) ELISA or 2) binding to H3-infected cells (FIG. 1, Panel B).

Example 2

Selection of a Higher- and Lower-Affinity B-Cell Clone

Figure 2:
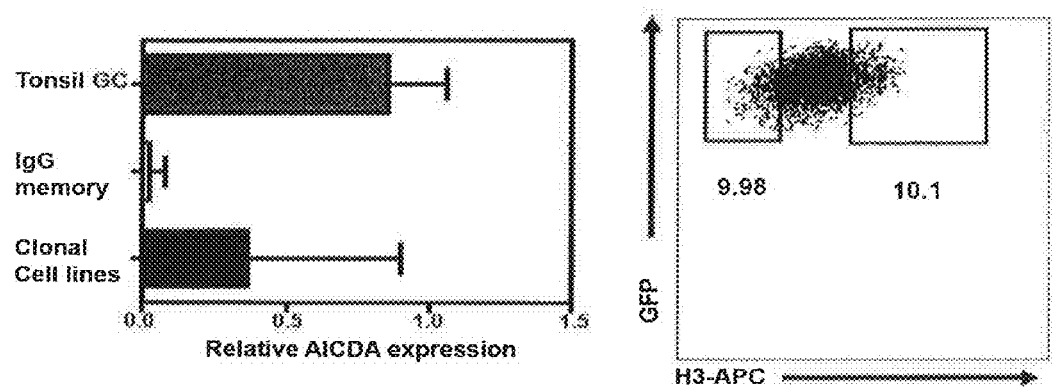
FIG. 2. Left Panel: mRNA levels of AICDA in CD19+ CD38+CD2O+IgD-tonsillar GC B-cells and CD19+IgG+ CD27+ peripheral blood memory B-cells compared to 23 BCL6- and Bcl-xL-transduced monoclonal cell lines. Right panel: Selection of high or low binding subclones within an H3-specific clone. Boxed populations were selected by cell sorting and further expanded.

Since the BCL6 Bcl-XL-transduced B-cells express the enzyme Activation Induced Deaminase (AID, gene nomenclature is AICDA) as described by Kwakkenbos et al. (FIG. 2, left panel, and "Generation of stable monoclonal antibody-producing B-cell receptor-positive human memory B-cells by genetic programming," Nature Medicine (2010) vol. 16 (1) pp. 123-8) an individual B-cell can make nucleotide changes in the immunoglobulin heavy and light chains. These changes may influence the binding affinity of the clones to its antigen. To determine if subclones of the HA H3 binding clone indeed can have a different binding profile, the H3-specific clone was again incubated with labeled HA H3 antigen. Using the FACS, a population of high HA H3 binding cells and a population of low HA H3 binding cells were sorted (FIG. 2, right panel) and maintained in culture for at least 13 days before the B-cell supernatant was harvested and tested.

Example 3

Figure 3:
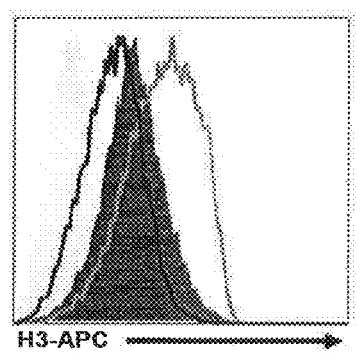
FIG. 3. Panel A: FACS analysis for the binding of labeled HA H3 to selected cells 13 days after their selection for higher or lower H3 BCR binding from a clonal cell. Increased or lowered H3 binding is maintained and stable after subcloning. Panel B: FACS staining for the BCR of the different selected subpopulations. Increased or lowered levels of H3 binding to selected populations correlates with the BCR expression on the cell surface of these populations. Light grey line: B-cells selected for high H3 binding; filled graph: B-cells not selected (parental cells); dark grey line: B-cells selected for low H3 binding.
Figure 3:
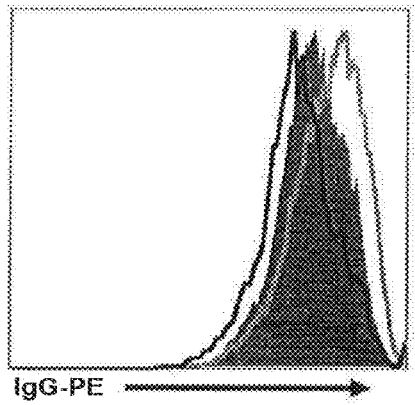

HA H3 High- and Low-Affinity Sorted B-Cells Express a Stable but Variable Level of Surface Immunoglobulin First, we characterized the stability of the sorted cells by analyzing the binding capacity of the B-cell receptor (BCR) to labeled HA H3 by FACS (FIG. 3, Panel A). Since the HA H3 high sorted cells still showed higher binding abilities, we next determined the surface immunoglobulin expression level by FACS (FIG. 3, Panel B). It was observed that the cells sorted for a relatively low binding capacity to HA H3 did express less immunoglobulin protein on the surface compared to cells sorted for high HA binding. This higher or lower BCR expression and BCR binding to HA H3 protein was maintained over time and became even more pronounced after a second round of sorting (data not shown).

Example 4

Figure 4:
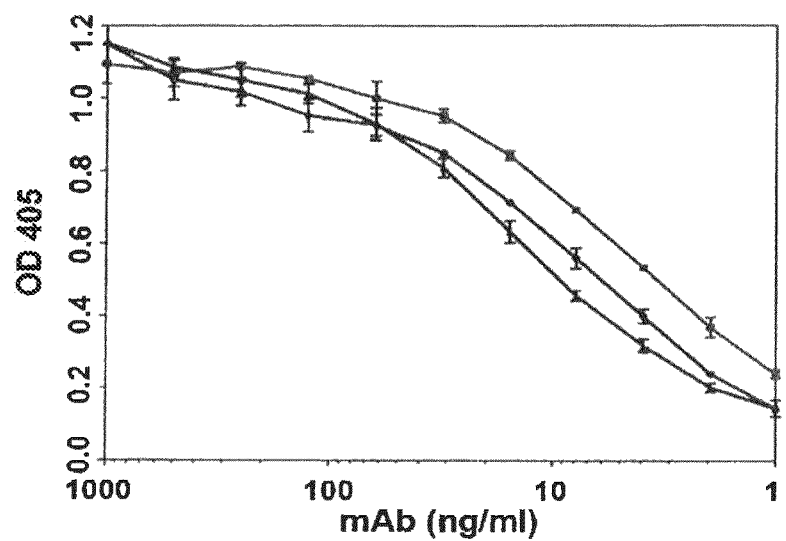
FIG. 4. H3 ELISA of the culture supernatant of the different (sub)populations. Secreted IgG from cells that were selected for higher binding to H3-APC protein show increased binding in the H3 ELISA compared to IgG from the non-sorted parental line. Top line: B-cells selected for high H3 binding; middle line: B-cells not selected (parental cells); bottom line: B-cells selected for low H3 binding.

Affinity for HA H3 of the Antibodies Derived from the Original and High and Low Affinity HA H3 Binding Cells To determine the binding affinity of the antibodies produced by the different HA H3-recognizing B-cells, the culture supernatant of the day 13 cultures of the original HA H3 binding cells and of the high- and low-affinity HA H3 binding cells was analyzed by ELISA. HA H3 (1 µg/ml Protein Sciences) was coated directly on the plate before the wells were incubated with the different B-cell supernatants. Binding of the human IgGs to the HA H3 protein was detected with an anti-human polyclonal goat antibody that was HRP labeled. Secreted IgG from cells that were selected for higher binding to H3-APC protein show increased binding in the H3 ELISA compared to IgG from the non-sorted parental line (FIG. 4).

Example 5

Combined BCR—Antigen Stain for the Selection of High and Low Affinity Clones

Figure 5:
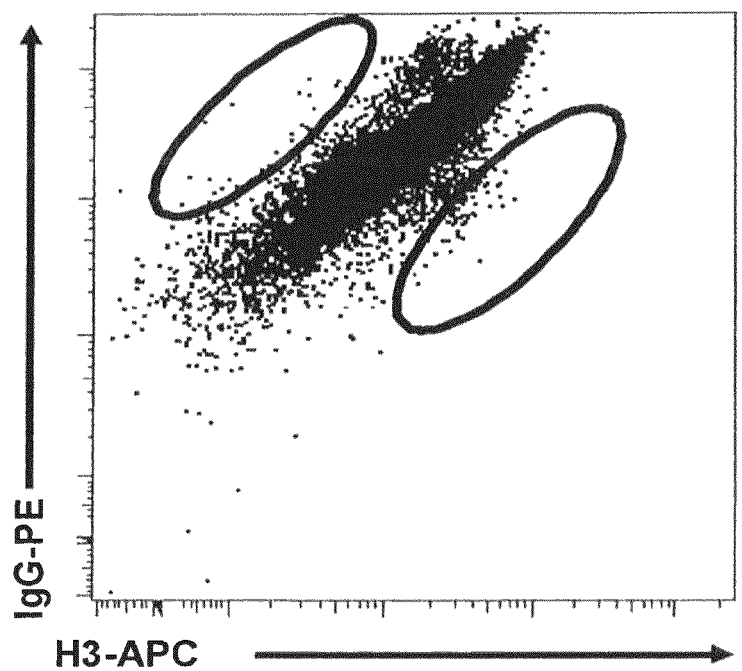
FIG. 5. Selection of high- or low-affinity subclones within an H3-specific clone (AT10_004). Cells were stained with Alexa-647 labeled HA H3 antigen together with IgG-PE antibody. Circled populations were selected by cell sorting and further expanded.

In Examples 2 and 3, it is shown that selection of B cells, within the heterogeneous subpopulation of a monoclonal B-cell clone, with the highest level of H3 binding may select for cells that have elevated levels of BCR expression. Thus, when selection is done solely based on the level of H3 binding, cells that have increased antigen affinity but low levels of BCR expression might be excluded. To exclude the influence of the level of immunoglobulin expression on the selection of high-affinity clones, a new set of selection rounds were performed using a combination of antigen staining (H3-Alexa-647) and BCR staining (FIG. 5). BCR staining was performed with antibodies that bind to the heavy or the light chain of the BCR. High H3 staining and low BCR staining indicates high antigen affinity, whereas low H3 staining and high BCR staining indicates low antigen affinity.

Figure 6:
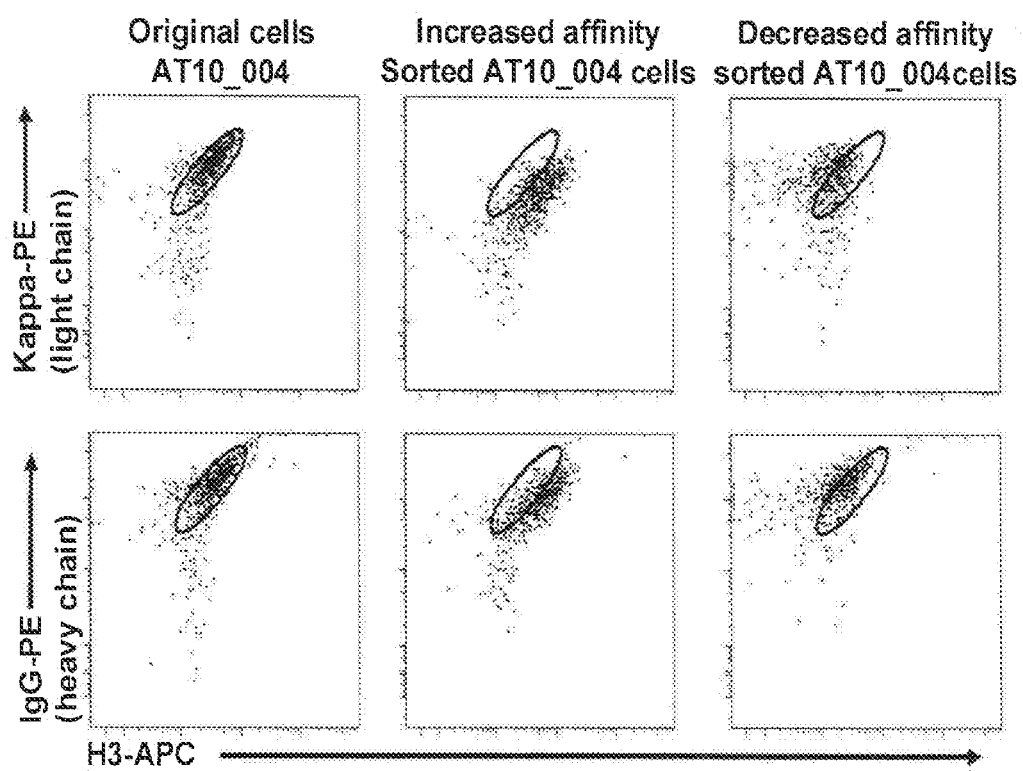
FIG. 6. FACS analysis for the binding of labeled HA H3 together with a BCR stain (either for the heavy chain, IgG-PE, or for the light chain, Kappa-PE) to selected cells two weeks after the third selection round for higher or lower H3 BCR binding and to the parental AT10_004.

An HA H3 specific B cell clone (AT10_004) was cultured for 2-3 weeks to produce millions of cells before an antigen-BCR staining was performed. Cells that showed deviating antigen affinity, both positive and negative, were selected and sorted on a cell sorter. After three rounds of sorting and growing, FACS analysis was performed on these cells to determine differences in antigen binding. Cells that were sorted three times for increased or decreased antigen binding show a clear shift in antigen binding compared to non-selected cells (FIG. 6). FIG. 6 demonstrates that increased or lowered H3 binding is maintained and stable after selection.

Example 6

Sequencing of the BCR from Selected Cells

We isolated total RNA with the RNeasy® mini kit (Qiagen) from AT10_004 and AT10_004 mutant B-cell cultures selected for high or low affinity, generated cDNA from the RNA, performed PCR and analyzed the sequence of the heavy chain and light chain of the BCR. A mutation leading to an amino acid change at position 38 (CDR1), resulting in the exchange of the Glycine to an Alanine in the heavy chain, was found for the cells that were sorted for decreased affinity (hereafter named "mutant A"). Mutations leading to amino acid changes in the light chain (compared to the parental AT10_004 sequence) were found for the increased affinity sorted cells. Sequence analysis showed a change of amino acid 108 (CDR3) in the kappa light chain from a Serine to a Tyrosine (hereafter named "mutant B"). An additional mutation at position 38 leading to replacement of Tyrosine to a Phenylalanine was found in some sequences (hereafter named "mutant C") (FIG. 7 and Table 1). To produce recombinant AT10_004 and increased affinity, mutants B and C mAb, we cloned the heavy and light variable regions in frame with human IgG1 and Kappa constant regions into a pcDNA3.1 (Invitrogen) based vector and transiently transfected 293T cells. We purified recombinant mAb from the culture supernatant with an AKTA (GE healthcare).

Example 7

Surface Plasmon Resonance (SPR) Analysis

SPR analysis was performed on an IBIS MX96 SPR imaging system (IBIS Technologies BV., Enschede, The Netherlands) as described (Lokate et al., 2007, J. Am. Chem. Soc. 129:14013-140318). In short, one SPR analysis cycle consists of one or more incubation steps in which analytes are flushed over a coated sensor, followed by a regeneration step, in which any bound analyte is removed from the sensor. Multiple cycles can be performed in one experiment.

Dilution series (concentration ranging from 0.30 to 10 µg/ml) of AT10_004 and AT10_004 mutant antibody in coupling buffer (PBS+0.03% Tween20+0.01 mg/ml BSA) were immobilized during 99 minutes on a human-IgG-specific gold-film gel-type SPR-chip (Ssens, Enschede, The Netherlands) using a continuous flow microspotter device (Wasatch Microfluidics, Salt Lake City, Utah, USA). After spotting, the sensor was washed three times with PBS+0.03% Tween20 (PBST).

Figure 8:
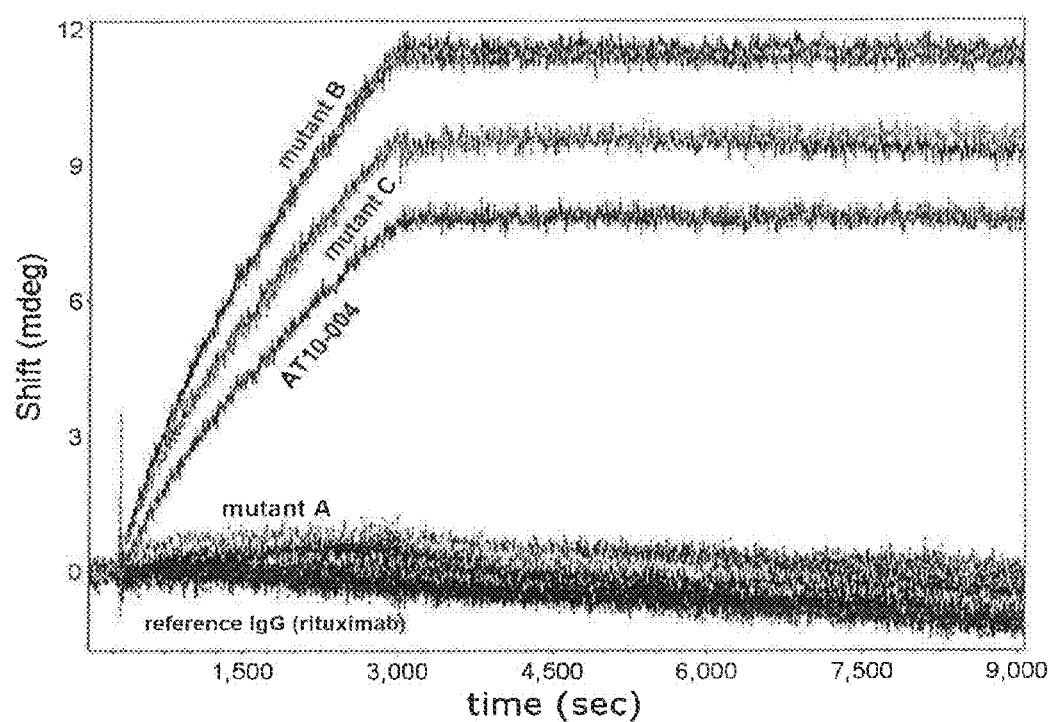
FIG. 8. SPR analysis of the binding of AT10_004 antibodies to HA H3. Association curves of antibodies AT10_004, AT10_004 mutant A, AT10_004 mutant B and AT10_004 mutant C.

To block any unoccupied sites in the anti-IgG coated SPR chip, the chip was first injected with a non-specific human IgG (rituximab, 10 µg/ml in PBST) and incubated for 45 minutes, followed by 100 minutes incubation with PBST. After this blocking step, two blank injection cycles were done, each consisting of 45 minutes injection with empty assay buffer (1×PBST+0.01% BSA) followed by 100 minutes incubation with PBST. Then, the sensor was injected with 1 µg/ml recombinant influenza HA3-protein (from H3N2, Wyoming, March 2003, Sino Biological Inc., Beijing, P.R. China) in assay buffer and incubated for 45 minutes. Subsequently, the sensor is washed with PBST and incubated for 100 minutes (to measure complex dissociation). Obtained data was analyzed using Sprint software (version 1.6.8.0, IBIS Technologies BV., Enschede, The Netherlands). Binding constants were fitted using Scrubber2 software (Biologic Software, Campbell, Australia). FIG. 8 shows that recombinant HA3 does not associate with AT10_004 mutant A. An increased association rate of HA3 for AT10_004 mutants B and C is seen compared to the non-mutated AT10_004. The binding constants obtained for AT10_004 and each mutant are shown in Table 2.

Example 8

Antibody Binding to Virus-Infected Cells

Figure 9:
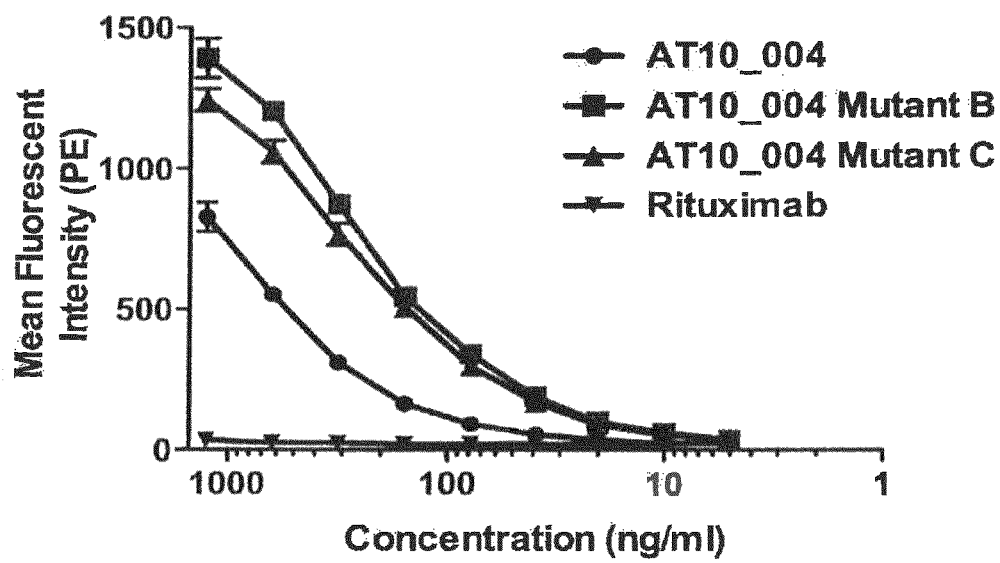
FIG. 9. Mean fluorescent intensity (MFI) of AT10_004 antibody variants binding to H3N2-infected cells in a FACS assay. Different concentrations of recombinant AT10_004, AT10_004 mutant B, AT10_004 mutant C and Rituximab (negative control) were incubated with H3N2-infected cells. Antibody binding was detected with PE-labeled goat anti-human F(ab') 2. Plotted is the mean and the SEM of the MFI of the resulting PE signal.

To test the binding capacity of AT10_004 and the AT10_004 mutants to virus-infected cells, we performed FACS analysis on Influenza H3N2 (A/Netherlands/177/2008) infected cells. MDCK-SIAT cells were grown in a T175 culture flask to 80-100% confluency in DMEM/FCS/PS/G418. The cell layer was washed 2× with 10 ml PBS after which 15 ml of Optimem/PS/G418/Trypsin was added. Subsequently, 0.5 ml of 100,000 TCID50 Influenza virus was added to the flask and cells were cultured at 37° C. After 24-48 hours, the cells were washed 2× with 10 ml PBS and detached from the plastic using Trypsin-EDTA. Cells were counted and frozen at −150° C. until use. The infected cells were defrosted and incubated with AT10_004 (mutant) antibodies or Rituximab (as negative control) at several concentrations for 30 minutes at 4° C. and then washed 2× with 150 µl PBS/2% FCS. Antibody binding was detected with anti-human IgG-PE (Southern Biotech) and analyzed on a Guava easyCyte 8HT, Millipore). AT10_004 mutants B and C both show increased staining intensity on H3N2-infected cells compared to the parental AT10_004 antibody (FIG. 9).

TABLE 1

Amino acid and nucleotide sequences of antibodies AT10-004 and AT10-004 mutants A, B and C. In the mutant sequences, mutations as compared to antibody AT10-004 are indicated in bold and underlined

| SEQ ID NO | Antibody | Identity | Sequence |
|---|---|---|---|
| 1 | AT10_004 | Heavy chain CDR1 | RHGIS |

TABLE 1-continued

Amino acid and nucleotide sequences of antibodies AT10-004 and AT10-004 mutants A, B and C. In the mutant sequences, mutations as compared to antibody AT10-004 are indicated in bold and underlined

| SEQ ID NO | Antibody | Identity | Sequence |
|---|---|---|---|
| 2 | AT10_004 | Heavy chain CDR2 | WISAYTGDTDYAQKFQG |
| 3 | AT10_004 | Heavy chain CDR3 | LRLQGEVVVPPSQSNWFDP |
| 4 | AT10_004 | Light chain CDR1 | RASQSVSRYLA |
| 5 | AT10_004 | Light chain CDR2 | DASNRAT |
| 6 | AT10_004 | Light chain CDR3 | QQRSNWLK |
| 7 | AT10_004 | Heavy chain | QVQLVQSGAEVRKPGASVKVSCKASGYTFTRHGISWVRQAPGQGLEWMGWISAYTGD TDYAQKFQGRVTMTTDTSTNTAYMELRSLRSDDAAVYYCARLRLQGEVVVPPSQSNW FDPWGQGTLVTVSS |
| 8 | AT10_004 | Light chain | EIVLTQSPATLSLYPGERATLSCRASQSVSRYLAWYQQKPGQAPRLLIYDASNRATGIPA RFSGSGSGTDFTLTISSLEPEDFAVYYCQQRSNWLKITFGQGTRLEIKGTV |
| 9 | AT10_004 | Heavy chain CDR1 | agg cat ggt atc agc |
| 10 | AT10_004 | Heavy chain CDR2 | tgg atc agc gct tac act ggt gac aca gac tat gca cag aaa ttc cag ggg |
| 11 | AT10_004 | Heavy chain CDR3 | ctt cgt ttg cag ggt gaa gtg gtg gtc cct cct agt caa tcc aat tgg ttc gac ccc |
| 12 | AT10_004 | Light chain CDR1 | agg gcc agt cag agt gtt agc agg tac tta gcc |
| 13 | AT10_004 | Light chain CDR2 | gat gca tcc aac agg gcc act |
| 14 | AT10_004 | Light chain CDR3 | cag cag cgt agc aac tgg ctt aag |
| 15 | AT10_004 | Heavy chain | cag gtt cag ctg gtg cag tct gga gct gag gtg agg aag cct ggg gcc tca gtg aag gtc tcc tgc aag gct tcc ggt tac acg ttt acc agg cat ggt atc agc tgg gtg cga cag gcc cct gga caa ggg ctt gag tgg atg gga tgg atc agc gct tac act ggt gac aca gac tat gca cag aaa ttc cag ggg cga gtc acc atg acc aca gat aca tcc acg aac aca gcc tac atg gaa ctg agg agc ctg aga tct gac gac gcg gcc gta tat tac tgt gcg aga ctt cgt ttg cag ggt gaa gtg gtg gtc cct cct agt caa tcc aat tgg ttc gac ccc tgg ggc cag gga acc ctg gtc acc gtc tcc tca |
| 16 | AT10_004 | Light chain | gaa att gtg ttg aca cag tct cca gcc acc ctg tct ttg tat cca ggg gaa aga gcc acc ctc tct tgc agg gcc agt cag agt gtt agc agg tac tta gcc tgg tac caa cag aaa cct ggc cag gct ccc agg ctc ctc atc tat gat gca tcc aac agg gcc act ggc atc cca gcc agg ttc agt ggc agt ggg tct ggg aca gac ttc acc ctc acc atc agc agc cta gag cct gaa gat ttt gca gtt tat tac tgt cag cag cgt gac aac tgg ctt aag atc acc ttc ggc caa ggg aca cga ctg gaa att aaa gga act gtg |
| 17 | AT10_004 mutant A | Heavy chain CDR1 | RHAIS |
| 18 | AT10_004 mutant A | Heavy chain CDR2 | WISAYTGDTDYAQKFQG |
| 19 | AT10_004 mutant A | Heavy chain CDR3 | LRLQGEVVVPPSQSNWFDP |
| 20 | AT10_004 mutant A | Light chain CDR1 | RASQSVSRYLA |
| 21 | AT10_004 mutant A | Light chain CDR2 | DASNRAT |

TABLE 1-continued

Amino acid and nucleotide sequences of antibodies AT10-004 and AT10-004 mutants A, B and C. In the mutant sequences, mutations as compared to antibody AT10-004 are indicated in bold and underlined

| SEQ ID NO | Antibody | Identity | Sequence |
|---|---|---|---|
| 22 | AT10_004 mutant A | Light chain CDR3 | QQRSNWLK |
| 23 | AT10_004 mutant A | Heavy chain | QVQLVQSGAEVRKPGASVKVSCKASGYTFTRHAISWVRQAPGQGLEWMGWISAYTGDTDYAQKFQGRVTMTTDTSTNTAYMELRSLRSDDAAVYYCARLRLQGEVVVPPSQSNWFDPWGQGTLVTVSS |
| 24 | AT10_004 mutant A | Light chain | EIVLTQSPATLSLYPGERATLSCRASQSVSRYLAWYQQKPGQAPRLLIYDASNRATGIPARFSGSGSGTDFTLTISSLEPEDFAVYYCQQRSNWLKITFGQGTRLEIKGTV |
| 25 | AT10_004 mutant A | Heavy chain CDR1 | agg cat gct atc agc |
| 26 | AT10_004 mutant A | Heavy chain CDR2 | tgg atc agc gct tac act ggt gac aca gac tat gca cag aaa ttc cag ggg |
| 27 | AT10_004 mutant A | Heavy chain CDR3 | ctt cgt ttg cag ggt gaa gtg gtg gtc cct cct agt caa tcc aat tgg ttc gac ccc |
| 28 | AT10_004 mutant A | Light chain CDR1 | agg gcc agt cag agt gtt agc agg tac tta gcc |
| 29 | AT10_004 mutant A | Light chain CDR2 | gat gca tcc aac agg gcc act |
| 30 | AT10_004 mutant A | Light chain CDR3 | cag cag cgt agc aac tgg ctt aag |
| 31 | AT10_004 mutant A | Heavy chain | cag gtt cag ctg gtg cag tct gga gct gag gtg agg aag cct ggg gcc tca gtg aag gtc tcc tgc aag gct tcc ggt tac acg ttt acc agg cat gct atc agc tgg gtg cga cag gcc cct gga caa ggg ctt gag tgg atg gga tgg atc agc gct tac act ggt gac aca gac tat gca cag aaa ttc cag ggg cga gtc acc atg acc aca gat aca tcc acg aac aca gcc tac atg gaa ctg agg agc ctg aga tct gac gac gcg gcc gta tat tac tgt gcg aga ctt cgt ttg cag ggt gaa gtg gtg gtc cct cct agt caa tcc aat tgg ttc gac ccc tgg ggc cag gga acc ctg gtc acc gtc tcc tca |
| 32 | AT10_004 mutant A | Light chain | gaa att gtg ttg aca cag tct cca gcc acc ctg tct ttg tat cca ggg gaa aga gcc acc ctc tct tgc agg gcc agt cag agt gtt agc agg tac tta gcc tgg tac caa cag aaa cct ggc cag gct ccc agg ctc ctc atc tat gat gca tcc aac agg gcc act ggc atc cca gcc agg ttc agt ggc agt ggg tct ggg aca gac ttc acc ctc acc atc agc agc cta gag cct gaa gat ttt gca gtt tat tac tgt cag cag cgt agc aac tgg ctt aag atc acc ttc ggc caa ggg aca cga ctg gaa att aaa gga act gtg |
| 33 | AT10_004 mutant B | Heavy chain CDR1 | RHGIS |
| 34 | AT10_004 mutant B | Heavy chain CDR2 | WISAYTGDTDYAQKFQG |
| 35 | AT10_004 mutant B | Heavy chain CDR3 | LRLQGEVVVPPSQSNWFDP |
| 36 | AT10_004 mutant B | Light chain CDR1 | RASQSVSRYLA |
| 37 | AT10_004 mutant B | Light chain CDR2 | DASNRAT |
| 38 | AT10_004 mutant B | Light chain CDR3 | QQRYNWLK |
| 39 | AT10_004 mutant B | Heavy chain | QVQLVQSGAEVRKPGASVKVSCKASGYTFTRHGISWVRQAPGQGLEWMGWISAYTGDTDYAQKFQGRVTMTTDTSTNTAYMELRSLRSDDAAVYYCARLRLQGEVVVPPSQSNWFDPWGQGTLVTVSS |
| 40 | AT10_004 mutant B | Light chain | EIVLTQSPATLSLYPGERATLSCRASQSVSRYLAWYQQKPGQAPRLLIYDASNRATGIPARFSGSGSGTDFTLTISSLEPEDFAVYYCQQRYNWLKITFGQGTRLEIKGTV |
| 41 | AT10_004 mutant B | Heavy chain CDR1 | agg cat ggt atc agc |

TABLE 1-continued

Amino acid and nucleotide sequences of antibodies AT10-004 and AT10-004 mutants A, B and C. In the mutant sequences, mutations as compared to antibody AT10-004 are indicated in bold and underlined

| SEQ ID NO | Antibody | Identity | Sequence |
|---|---|---|---|
| 42 | AT10_004 mutant B | Heavy chain CDR2 | tgg atc agc gct tac act ggt gac aca gac tat gca cag aaa ttc agg ggg |
| 43 | AT10_004 mutant B | Heavy chain CDR3 | ctt cgt ttg cag ggt gaa gtg gtg gtc cct cct agt caa tcc aat tgg ttc gac ccc |
| 44 | AT10_004 mutant B | Light chain CDR1 | agg gcc agt cag agt gtt agc agg tac tta gcc |
| 45 | AT10_004 mutant B | Light chain CDR2 | gat gca tcc aac agg gcc act |
| 46 | AT10_004 mutant B | Light chain CDR3 | cag cag cgt tac aac tgg ctt aag |
| 47 | AT10_004 mutant B | Heavy chain | cag gtt cag ctg gtg cag tct gga gct gag gtg agg aag cct ggg gcc tca gtg aag gtc tcc tgc aag gct tcc ggt tac acg ttt acc agg cat ggt atc agc tgg gtg cga cag gcc cct gga caa ggg ctt gag tgg atg gga tgg atc agc gct tac act ggt gac aca gac tat gca cag aaa ttc agg ggg cga gtc acc atg acc aca gat aca tcc acg aac aca gcc tac atg gaa ctg agg agc ctg aga tct gac gac gcg gcc gta tat tac tgt gcg aga ctt cgt ttg cag ggt gaa gtg gtg gtc cct cct agt caa tcc aat tgg ttc gac ccc tgg ggc cag gga acc ctg gtc acc gtc tcc tca |
| 48 | AT10_004 mutant B | Light chain | gaa att gtg ttg aca cag tct cca gcc acc ctg tct ttg tat cca ggg gaa aga gcc acc ctc tct tgc agg gcc agt cag agt gtt agc agg tac tta gcc tgg tac caa cag aaa cct ggc cag gct ccc agg ctc ctc atc tat gat gca tcc aac agg gcc act ggc atc cca gcc agg ttc agt ggc agt ggg tct ggg aca gac ttc acc ctc acc atc agc agc cta gag cct gaa gat ttt gca gtt tat tac tgt cag cag cgt tac aac tgg ctt aag atc acc ttc ggc caa ggg aca cga ctg gaa att aaa gga act gtg |
| 49 | AT10_004 mutant C | Heavy chain CDR1 | RHGIS |
| 50 | AT10_004 mutant C | Heavy chain CDR2 | WISAYTGDTDYAQKFQG |
| 51 | AT10_004 mutant C | Heavy chain CDR3 | LRLQGEVVVPPSQSNWFDP |
| 52 | AT10_004 mutant C | Light chain CDR1 | RASQSVSRFLA |
| 53 | AT10_004 mutant C | Light chain CDR2 | DASNRAT |
| 54 | AT10_004 mutant C | Light chain CDR3 | QQRYNWLK |
| 55 | AT10_004 mutant C | Heavy chain | QVQLVQSGAEVRKPGASVKVSCKASGYTFTRHGISWVRQAPGQGLEWMGWISAYTGDTDYAQKFQGRVTMTTDTSTNTAYMELRSLRSDDAAVYYCARLRLQGEVVVPPSQSNWFDPWGQGTLVTVSS |
| 56 | AT10_004 mutant C | Light chain | EIVLTQSPATLSLYPGERATLSCRASQSVSRYLAWYQQKPGQAPRLLIYDASNRATGIPARFSGSGSGTDFTLTISSLEPEDFAVYYCQQRYNWLKITFGQGTRLEIKGTV |
| 57 | AT10_004 mutant C | Heavy chain CDR1 | agg cat ggt atc agc |
| 58 | AT10_004 mutant C | Heavy chain CDR2 | tgg atc agc gct tac act ggt gac aca gac tat gca cag aaa ttc agg ggg |
| 59 | AT10_004 mutant C | Heavy chain CDR3 | ctt cgt ttg cag ggt gaa gtg gtg gtc cct cct agt caa tcc aat tgg ttc gac ccc |
| 60 | AT10_004 mutant C | Light chain CDR1 | agg gcc agt cag agt gtt agc agg ttc tta gcc |
| 61 | AT10_004 mutant C | Light chain CDR2 | gat gca tcc aac agg gcc act |

TABLE 1-continued

Amino acid and nucleotide sequences of antibodies AT10-004 and AT10-004 mutants A, B and C. In the mutant sequences, mutations as compared to antibody AT10-004 are indicated in bold and underlined

| SEQ ID NO | Antibody | Identity | Sequence |
|---|---|---|---|
| 62 | AT10_004 mutant C | Light chain CDR3 | cag cag cgt tac aac tgg ctt aag |
| 63 | AT10_004 mutant C | Heavy chain | cag gtt cag ctg gtg cag tct gga gct gag gtg agg aag cct ggg gcc tca gtg aag gtc tcc tgc aag gct tcc ggt tac acg ttt acc agg cat ggt atc agc tgg gtg cga cag gcc cct gga caa ggg ctt gag tgg atg gga tgg atc agc gct tac act ggt gac aca gac tat gca cag aaa ttc cag ggg cga gtc acc atg acc aca gat aca tcc acg aac aca gcc tac atg gaa ctg agg agc ctg aga tct gac gac gcg gcc gta tat tac tgt gcg aga ctt cgt ttg cag ggt gaa gtg gtg gtc cct cct agt caa tcc aat tgg ttc gac ccc tgg ggc cag gga acc ctg gtc acc gtc tcc tca |
| 64 | AT10_004 mutant C | Light chain | gaa att gtg ttg aca cag tct cca gcc acc ctg tct ttg tat cca ggg gaa aga gcc acc ctc tct tgc agg gcc agt cag agt gtt agc agg ttc tta gcc tgg tac caa cag aaa cct ggc cag gct ccc agg ctc ctc atc tat gat gca tcc aac agg gcc act ggc atc cca gcc agg ttc agt ggc agt ggg tct ggg aca gac ttc acc ctc acc atc agc agc cta gag cct gaa gat ttt gca gtt tat tac tgt cag cag cgt tac aac tgg ctt aag atc acc ttc ggc caa ggg aca cga ctg gaa att aaa gga act gtg |

TABLE 2

Binding constants for AT10-004 and mutants

| Antibody: | ha: | kd: | Kn: |
|---|---|---|---|
| AT10_004 | 1.4 (±0.1) | 0.1 | 70 (±10) |
| AT10_004, mutant A | 0 | — | — |
| AT10_004, mutant B | 1.9 (±0.1) | 0.1 | 50 (±10) |
| AT10_004, mutant C | 1.7 (±0.1) | 0.1 | 60 (±10) | ka in $10^4$ sec$^{-1}$ * M$^{-1}$,
kct in $10^{-5}$ sec$^{-1}$,
Ku in pM

Constants were fitted in Scrubber2, using a global fit to a 1:1 interaction model.

What is claimed is:

1. A selected antibody obtained by a method, said method comprising the steps of:
   a) selecting a B-cell able to produce said antibody, wherein said antibody is specific for an antigen of interest or selecting a B-cell able to differentiate into a B-cell that is able to produce said antibody, wherein said antibody is specific for an antigen of interest;
   b) inducing, enhancing and/or maintaining expression of BCL6 in said B-cell;
   c) inducing, enhancing and/or maintaining expression of an anti-apoptotic nucleic acid in said B-cell;
   d) allowing expansion of said B cells into a first population of B cells;
   e) performing antigen staining and BCR staining of B cells from said first population;
   f) selecting a chosen B cell from said first population of B cells that has a high antigen affinity;
   g) allowing expansion of said chosen B-cell into a population of chosen B-cells;
   h) measuring the antigen association rate and dissociation rate of antibodies produced by at least one chosen B-cell from said population of chosen B-cells; and
   i) selecting said selected antibody, said selected antibody having an affinity for said antigen of interest from said chosen B-cells that is higher than the average affinity of said first population of B-cells for said antigen of interest,
   wherein said antibody has heavy and light chain CDRs 1-3 comprising SEQ ID NO: 1-6, wherein the serine residue of the light chain CDR3 sequence in SEQ ID NO: 6 is replaced by tyrosine and the tyrosine residue of the light chain CDR1 sequence in SED ID NO: 4 is replaced with phenylalanine.

2. A selected antibody obtained by a method, said method comprising the steps of:
   a) selecting a B-cell, wherein said B-cell is able to produce an antibody specific for an antigen of interest or selecting a B-cell, wherein said B-cell is able to differentiate into a B-cell that is able to produce an antibody specific for an antigen of interest;
   b) inducing, enhancing and/or maintaining expression of BCL6 in said B-cell;
   c) inducing, enhancing and/or maintaining expression of an anti-apoptotic nucleic acid in said B-cell;
   d) allowing expansion of said B cells into a population of B cells;
   e) performing antigen staining and BCR staining of B cells from said population;
   f) selecting a chosen B cell that has a low antigen affinity;
   g) allowing expansion of said chosen B-cell into a population of chosen B-cells;
   h) measuring the antigen association rate and dissociation rate of antibodies produced by at least one chosen B-cell from said population of chosen B-cells; and
   i) selecting said selected antibody from said population of chosen B-cells, said selected antibody having with an affinity for said antigen of interest that is lower than the average affinity of said first population of B-cells for said antigen of interest,
   wherein said selected antibody has heavy and light chain CDRs 1-3 comprising SEQ ID NO: 1-6, wherein the glutamine residue of the heavy chain CDR1 sequence in SEQ ID NO: 1 is replaced by alanine.

3. An antibody or a functional part thereof, comprising the heavy chain CDR1 sequence RHGIS (SEQ ID NO:1), the heavy chain CDR2 sequence WISAYTGDTDYAQKFQG (SEQ ID NO:2), the heavy chain CDR3 sequence LRLQ-GEVVVPPSQSNWFDP (SEQ ID NO:3), the light chain CDR1 sequence RASQSVSRYLA (SEQ ID NO:4), the light chain CDR2 sequence DASNRAT (SEQ ID NO:5) and the light chain CDR3 sequence QQRYNWLK (SEQ ID NO:38).

4. An antibody or a functional part thereof, comprising the heavy chain CDR1 sequence RHGIS (SEQ ID NO:1), the heavy chain CDR2 sequence WISAYTGDTDYAQKFQG (SEQ ID NO:2), the heavy chain CDR3 sequence LRLQ-GEVVVPPSQSNWFDP (SEQ ID NO:3), the light chain CDR1 sequence RASQSVSRFLA (SEQ ID NO:52), the light chain CDR2 sequence DASNRAT (SEQ ID NO:5) and the light chain CDR3 sequence QQRYNWLK (SEQ ID NO:54).

5. An antibody or a functional part thereof, comprising the heavy chain CDR1 sequence RHAIS (SEQ ID NO:17, the heavy chain CDR2 sequence WISAYTGDTDYAQKFQG (SEQ ID NO:18), the heavy chain CDR3 sequence LRLQ-GEVVVPPSQSNWFDP (SEQ ID NO:19), the light chain CDR1 sequence RASQSVSRYLA (SEQ ID NO:20), the light chain CDR2 sequence DASNRAT (SEQ ID NO:21) and the light chain CDR3 sequence QQRSNWLK (SEQ ID NO:22).

6. The antibody or functional part of claim 3, wherein the antibody is an IgM, an IgG, an IgA or an IgE.

7. The antibody or a functional part of claim 4, wherein the antibody is an IgM, an IgG, an IgA or an IgE.

8. The antibody or a functional part of claim 5, wherein the antibody is an IgM, an IgG, an IgA or an IgE.

* * * * *

SEQUENCE LISTING

<160> NUMBER OF SEQ ID NOS: 64

<210> SEQ ID NO 1
<211> LENGTH: 5
<212> TYPE: PRT
<213> ORGANISM: Artificial
<220> FEATURE:
<223> OTHER INFORMATION: Synthetic Construct

<400> SEQUENCE: 1

Arg His Gly Ile Ser
1               5

<210> SEQ ID NO 2
<211> LENGTH: 17
<212> TYPE: PRT
<213> ORGANISM: Artificial
<220> FEATURE:
<223> OTHER INFORMATION: Synthetic Construct

<400> SEQUENCE: 2

Trp Ile Ser Ala Tyr Thr Gly Asp Thr Asp Tyr Ala Gln Lys Phe Gln
1               5                   10                  15

Gly

-continued

<210> SEQ ID NO 3
<211> LENGTH: 19
<212> TYPE: PRT
<213> ORGANISM: Artificial
<220> FEATURE:
<223> OTHER INFORMATION: Synthetic Construct

<400> SEQUENCE: 3

Leu Arg Leu Gln Gly Glu Val Val Pro Pro Ser Gln Ser Asn Trp
1               5                   10                  15

Phe Asp Pro

<210> SEQ ID NO 4
<211> LENGTH: 11
<212> TYPE: PRT
<213> ORGANISM: Artificial
<220> FEATURE:
<223> OTHER INFORMATION: Synthetic Construct

<400> SEQUENCE: 4

Arg Ala Ser Gln Ser Val Ser Arg Tyr Leu Ala
1               5                   10

<210> SEQ ID NO 5
<211> LENGTH: 7
<212> TYPE: PRT
<213> ORGANISM: Artificial
<220> FEATURE:
<223> OTHER INFORMATION: Synthetic Construct

<400> SEQUENCE: 5

Asp Ala Ser Asn Arg Ala Thr
1               5

<210> SEQ ID NO 6
<211> LENGTH: 8
<212> TYPE: PRT
<213> ORGANISM: Artificial
<220> FEATURE:
<223> OTHER INFORMATION: Synthetic Construct

<400> SEQUENCE: 6

Gln Gln Arg Ser Asn Trp Leu Lys
1               5

<210> SEQ ID NO 7
<211> LENGTH: 128
<212> TYPE: PRT
<213> ORGANISM: Artificial
<220> FEATURE:
<223> OTHER INFORMATION: Synthetic Construct

<400> SEQUENCE: 7

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Arg His
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asp Thr Asp Tyr Ala Gln Lys Phe
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Ala Ala Val Tyr Tyr Cys
                85                  90                  95

Ala Arg Leu Arg Leu Gln Gly Glu Val Val Pro Pro Ser Gln Ser
            100                 105                 110

Asn Trp Phe Asp Pro Trp Gly Gln Gly Thr Leu Val Thr Val Ser Ser
            115                 120                 125

<210> SEQ ID NO 8
<211> LENGTH: 111
<212> TYPE: PRT
<213> ORGANISM: Artificial
<220> FEATURE:
<223> OTHER INFORMATION: Synthetic Construct

<400> SEQUENCE: 8

Glu Ile Val Leu Thr Gln Ser Pro Ala Thr Leu Ser Leu Tyr Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Leu Lys
                85                  90                  95

Ile Thr Phe Gly Gln Gly Thr Arg Leu Glu Ile Lys Gly Thr Val
            100                 105                 110

<210> SEQ ID NO 9
<211> LENGTH: 15
<212> TYPE: DNA
<213> ORGANISM: Artificial
<220> FEATURE:
<223> OTHER INFORMATION: Antibody AT10-004 and AT10-004 mutants

<400> SEQUENCE: 9
aggcatggta tcagc                                                15

<210> SEQ ID NO 10
<211> LENGTH: 51
<212> TYPE: DNA
<213> ORGANISM: Artificial
<220> FEATURE:
<223> OTHER INFORMATION: Antibody AT10-004 and AT10-004 mutants

<400> SEQUENCE: 10
tggatcagcg cttacactgg tgacacagac tatgcacaga aattccaggg g         51

<210> SEQ ID NO 11
<211> LENGTH: 57
<212> TYPE: DNA
<213> ORGANISM: Artificial
<220> FEATURE:
<223> OTHER INFORMATION: Antibody AT10-004 and AT10-004 mutants

<400> SEQUENCE: 11
cttcgtttgc agggtgaagt ggtggtccct cctagtcaat ccaattggtt cgacccc    57

```
<210> SEQ ID NO 12
<211> LENGTH: 33
<212> TYPE: DNA
<213> ORGANISM: Artificial
<220> FEATURE:
<223> OTHER INFORMATION: Antibody AT10-004 and AT10-004 mutants

<400> SEQUENCE: 12
agggccagtc agagtgttag caggtactta gcc                              33

<210> SEQ ID NO 13
<211> LENGTH: 21
<212> TYPE: DNA
<213> ORGANISM: Artificial
<220> FEATURE:
<223> OTHER INFORMATION: Antibody AT10-004 and AT10-004 mutants

<400> SEQUENCE: 13
gatgcatcca acagggccac t                                           21

<210> SEQ ID NO 14
<211> LENGTH: 24
<212> TYPE: DNA
<213> ORGANISM: Artificial
<220> FEATURE:
<223> OTHER INFORMATION: Antibody AT10-004 and AT10-004 mutants

<400> SEQUENCE: 14
cagcagcgta gcaactggct taag                                        24

<210> SEQ ID NO 15
<211> LENGTH: 384
<212> TYPE: DNA
<213> ORGANISM: Artificial
<220> FEATURE:
<223> OTHER INFORMATION: Antibody AT10-004 and AT10-004 mutants

<400> SEQUENCE: 15
caggttcagc tggtgcagtc tggagctgag gtgaggaagc ctggggcctc agtgaaggtc   60
tcctgcaagg cttccggtta cacgtttacc aggcatggta tcagctgggt gcgacaggcc  120
cctggacaag gcttgagtg gatgggatgg atcagcgctt acactggtga cacagactat   180
gcacagaaat tccaggggcg agtcaccatg accacagata catccacgaa cacagcctac  240
atggaactga ggagcctgag atctgacgac gcggccgtat attactgtgc gagacttcgt  300
ttgcagggtg aagtggtggt ccctcctagt caatccaatt ggttcgaccc ctggggccag  360
ggaaccctgg tcaccgtctc ctca                                        384

<210> SEQ ID NO 16
<211> LENGTH: 333
<212> TYPE: DNA
<213> ORGANISM: Artificial
<220> FEATURE:
<223> OTHER INFORMATION: Antibody AT10-004 and AT10-004 mutants

<400> SEQUENCE: 16
gaaattgtgt tgacacagtc tccagccacc ctgtctttgt atccagggga aagagccacc   60
ctctcttgca gggccagtca gagtgttagc aggtacttag cctggtacca acagaaacct  120
ggccaggctc ccaggctcct catctatgat gcatccaaca gggccactgg catcccagcc  180
aggttcagtg gcagtgggtc tgggacagac ttcaccctca ccatcagcag cctagagcct  240
```

```
gaagattttg cagtttatta ctgtcagcag cgtgacaact ggcttaagat caccttcggc    300
caagggacac gactggaaat taaaggaact gtg                                 333
```

<210> SEQ ID NO 17
<211> LENGTH: 5
<212> TYPE: PRT
<213> ORGANISM: Artificial
<220> FEATURE:
<223> OTHER INFORMATION: Synthetic Construct

<400> SEQUENCE: 17

Arg His Ala Ile Ser
1               5

<210> SEQ ID NO 18
<211> LENGTH: 17
<212> TYPE: PRT
<213> ORGANISM: Artificial
<220> FEATURE:
<223> OTHER INFORMATION: Synthetic Construct

<400> SEQUENCE: 18

Trp Ile Ser Ala Tyr Thr Gly Asp Thr Asp Tyr Ala Gln Lys Phe Gln
1               5                   10                  15

Gly

<210> SEQ ID NO 19
<211> LENGTH: 19
<212> TYPE: PRT
<213> ORGANISM: Artificial
<220> FEATURE:
<223> OTHER INFORMATION: Synthetic Construct

<400> SEQUENCE: 19

Leu Arg Leu Gln Gly Glu Val Val Pro Ser Gln Ser Asn Trp
1               5                   10                  15

Phe Asp Pro

<210> SEQ ID NO 20
<211> LENGTH: 11
<212> TYPE: PRT
<213> ORGANISM: Artificial
<220> FEATURE:
<223> OTHER INFORMATION: Synthetic Construct

<400> SEQUENCE: 20

Arg Ala Ser Gln Ser Val Ser Arg Tyr Leu Ala
1               5                   10

<210> SEQ ID NO 21
<211> LENGTH: 7
<212> TYPE: PRT
<213> ORGANISM: Artificial
<220> FEATURE:
<223> OTHER INFORMATION: Synthetic Construct

<400> SEQUENCE: 21

Asp Ala Ser Asn Arg Ala Thr
1               5

<210> SEQ ID NO 22
<211> LENGTH: 8
<212> TYPE: PRT
<213> ORGANISM: Artificial

```
<220> FEATURE:
<223> OTHER INFORMATION: Synthetic Construct

<400> SEQUENCE: 22

Gln Gln Arg Ser Asn Trp Leu Lys
1               5

<210> SEQ ID NO 23
<211> LENGTH: 128
<212> TYPE: PRT
<213> ORGANISM: Artificial
<220> FEATURE:
<223> OTHER INFORMATION: Synthetic Construct

<400> SEQUENCE: 23

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Arg His
            20                  25                  30

Ala Ile Ser Trp Val Arg Gln Ala Pro Gly Gln Gly Leu Glu Trp Met
        35                  40                  45

Gly Trp Ile Ser Ala Tyr Thr Gly Asp Thr Asp Tyr Ala Gln Lys Phe
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Ala Ala Val Tyr Tyr Cys
                85                  90                  95

Ala Arg Leu Arg Leu Gln Gly Glu Val Val Pro Pro Ser Gln Ser
            100                 105                 110

Asn Trp Phe Asp Pro Trp Gly Gln Gly Thr Leu Val Thr Val Ser Ser
        115                 120                 125

<210> SEQ ID NO 24
<211> LENGTH: 111
<212> TYPE: PRT
<213> ORGANISM: Artificial
<220> FEATURE:
<223> OTHER INFORMATION: Synthetic Construct

<400> SEQUENCE: 24

Glu Ile Val Leu Thr Gln Ser Pro Ala Thr Leu Ser Leu Tyr Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Leu Lys
                85                  90                  95

Ile Thr Phe Gly Gln Gly Thr Arg Leu Glu Ile Lys Gly Thr Val
            100                 105                 110

<210> SEQ ID NO 25
<211> LENGTH: 15
<212> TYPE: DNA
<213> ORGANISM: Artificial
```

<220> FEATURE:
<223> OTHER INFORMATION: Antibody AT10-004 and AT10-004 mutants

<400> SEQUENCE: 25
aggcatgcta tcagc                                                    15

<210> SEQ ID NO 26
<211> LENGTH: 51
<212> TYPE: DNA
<213> ORGANISM: Artificial
<220> FEATURE:
<223> OTHER INFORMATION: Antibody AT10-004 and AT10-004 mutants

<400> SEQUENCE: 26
tggatcagcg cttacactgg tgacacagac tatgcacaga aattccaggg g            51

<210> SEQ ID NO 27
<211> LENGTH: 57
<212> TYPE: DNA
<213> ORGANISM: Artificial
<220> FEATURE:
<223> OTHER INFORMATION: Antibody AT10-004 and AT10-004 mutants

<400> SEQUENCE: 27
cttcgtttgc agggtgaagt ggtggtccct cctagtcaat ccaattggtt cgacccc      57

<210> SEQ ID NO 28
<211> LENGTH: 33
<212> TYPE: DNA
<213> ORGANISM: Artificial
<220> FEATURE:
<223> OTHER INFORMATION: Antibody AT10-004 and AT10-004 mutants

<400> SEQUENCE: 28
agggccagtc agagtgttag caggtactta gcc                                33

<210> SEQ ID NO 29
<211> LENGTH: 21
<212> TYPE: DNA
<213> ORGANISM: Artificial
<220> FEATURE:
<223> OTHER INFORMATION: Antibody AT10-004 and AT10-004 mutants

<400> SEQUENCE: 29
gatgcatcca acagggccac t                                             21

<210> SEQ ID NO 30
<211> LENGTH: 21
<212> TYPE: DNA
<213> ORGANISM: Artificial
<220> FEATURE:
<223> OTHER INFORMATION: Antibody AT10-004 and AT10-004 mutants

<400> SEQUENCE: 30
cagcagcgta gcaactggaa g                                             21

<210> SEQ ID NO 31
<211> LENGTH: 384
<212> TYPE: DNA
<213> ORGANISM: Artificial
<220> FEATURE:
<223> OTHER INFORMATION: Antibody AT10-004 and AT10-004 mutants

<400> SEQUENCE: 31

```
caggttcagc tggtgcagtc tggagctgag gtgaggaagc ctggggcctc agtgaaggtc    60
tcctgcaagg cttccggtta cacgtttacc aggcatgcta tcagctgggt gcgacaggcc   120
cctggacaag ggcttgagtg gatgggatgg atcagcgctt acactggtga cacagactat   180
gcacagaaat tccaggggcg agtcaccatg accacagata catccacgaa cacagcctac   240
atggaactga ggagcctgag atctgacgac gcggccgtat attactgtgc gagacttcgt   300
ttgcagggtg aagtggtggt ccctcctagt caatccaatt ggttcgaccc ctggggccag   360
ggaaccctgg tcaccgtctc ctca                                          384
```

<210> SEQ ID NO 32
<211> LENGTH: 333
<212> TYPE: DNA
<213> ORGANISM: Artificial
<220> FEATURE:
<223> OTHER INFORMATION: Antibody AT10-004 and AT10-004 mutants

<400> SEQUENCE: 32

```
gaaattgtgt tgacacagtc tccagccacc ctgtctttgt atccagggga agagccacc    60
ctctcttgca gggccagtca gagtgttagc aggtacttag cctggtacca acagaaacct   120
ggccaggctc ccaggctcct catctatgat gcatccaaca gggccactgg catcccagcc   180
aggttcagtg gcagtgggtc tgggacagac ttcaccctca ccatcagcag cctagagcct   240
gaagattttg cagtttatta ctgtcagcag cgtagcaact ggcttaagat caccttcggc   300
caagggacac gactggaaat taaaggaact gtg                                333
```

<210> SEQ ID NO 33
<211> LENGTH: 5
<212> TYPE: PRT
<213> ORGANISM: Artificial
<220> FEATURE:
<223> OTHER INFORMATION: Synthetic Construct

<400> SEQUENCE: 33

Arg His Gly Ile Ser
1               5

<210> SEQ ID NO 34
<211> LENGTH: 17
<212> TYPE: PRT
<213> ORGANISM: Artificial
<220> FEATURE:
<223> OTHER INFORMATION: Synthetic Construct

<400> SEQUENCE: 34

Trp Ile Ser Ala Tyr Thr Gly Asp Thr Asp Tyr Ala Gln Lys Phe Gln
1               5                   10                  15

Gly

<210> SEQ ID NO 35
<211> LENGTH: 19
<212> TYPE: PRT
<213> ORGANISM: Artificial
<220> FEATURE:
<223> OTHER INFORMATION: Synthetic Construct

```
<400> SEQUENCE: 35

Leu Arg Leu Gln Gly Glu Val Val Pro Pro Ser Gln Ser Asn Trp
1               5                   10                  15

Phe Asp Pro

<210> SEQ ID NO 36
<211> LENGTH: 11
<212> TYPE: PRT
<213> ORGANISM: Artificial
<220> FEATURE:
<223> OTHER INFORMATION: Synthetic Construct

<400> SEQUENCE: 36

Arg Ala Ser Gln Ser Val Ser Arg Tyr Leu Ala
1               5                   10

<210> SEQ ID NO 37
<211> LENGTH: 7
<212> TYPE: PRT
<213> ORGANISM: Artificial
<220> FEATURE:
<223> OTHER INFORMATION: Synthetic Construct

<400> SEQUENCE: 37

Asp Ala Ser Asn Arg Ala Thr
1               5

<210> SEQ ID NO 38
<211> LENGTH: 8
<212> TYPE: PRT
<213> ORGANISM: Artificial
<220> FEATURE:
<223> OTHER INFORMATION: Synthetic Construct

<400> SEQUENCE: 38

Gln Gln Arg Tyr Asn Trp Leu Lys
1               5

<210> SEQ ID NO 39
<211> LENGTH: 128
<212> TYPE: PRT
<213> ORGANISM: Artificial
<220> FEATURE:
<223> OTHER INFORMATION: Synthetic Construct

<400> SEQUENCE: 39

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Arg His
                20                  25                  30

Gly Ile Ser Trp Val Arg Gln Ala Pro Gly Gln Gly Leu Glu Trp Met
            35                  40                  45

Gly Trp Ile Ser Ala Tyr Thr Gly Asp Thr Asp Tyr Ala Gln Lys Phe
        50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Ala Val Tyr Tyr Cys
                85                  90                  95

Ala Arg Leu Arg Leu Gln Gly Glu Val Val Pro Pro Ser Gln Ser
            100                 105                 110

Asn Trp Phe Asp Pro Trp Gly Gln Gly Thr Leu Val Thr Val Ser Ser
        115                 120                 125
```

<210> SEQ ID NO 40
<211> LENGTH: 111
<212> TYPE: PRT
<213> ORGANISM: Artificial
<220> FEATURE:
<223> OTHER INFORMATION: Synthetic Construct

<400> SEQUENCE: 40

```
Glu Ile Val Leu Thr Gln Ser Pro Ala Thr Leu Ser Leu Tyr Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Tyr Asn Trp Leu Lys
                85                  90                  95

Ile Thr Phe Gly Gln Gly Thr Arg Leu Glu Ile Lys Gly Thr Val
            100                 105                 110
```

<210> SEQ ID NO 41
<211> LENGTH: 15
<212> TYPE: DNA
<213> ORGANISM: Artificial
<220> FEATURE:
<223> OTHER INFORMATION: Antibody AT10-004 and AT10-004 mutants

<400> SEQUENCE: 41
aggcatggta tcagc                                                    15

<210> SEQ ID NO 42
<211> LENGTH: 51
<212> TYPE: DNA
<213> ORGANISM: Artificial
<220> FEATURE:
<223> OTHER INFORMATION: Antibody AT10-004 and AT10-004 mutants

<400> SEQUENCE: 42
tggatcagcg cttacactgg tgacacagac tatgcacaga aattccaggg g             51

<210> SEQ ID NO 43
<211> LENGTH: 57
<212> TYPE: DNA
<213> ORGANISM: Artificial
<220> FEATURE:
<223> OTHER INFORMATION: Antibody AT10-004 and AT10-004 mutants

<400> SEQUENCE: 43
cttcgtttgc agggtgaagt ggtggtccct cctagtcaat ccaattggtt cgacccc       57

<210> SEQ ID NO 44
<211> LENGTH: 33
<212> TYPE: DNA
<213> ORGANISM: Artificial
<220> FEATURE:
<223> OTHER INFORMATION: Antibody AT10-004 and AT10-004 mutants

<400> SEQUENCE: 44
agggccagtc agagtgttag caggtactta gcc                                 33

<210> SEQ ID NO 45
<211> LENGTH: 21
<212> TYPE: DNA
<213> ORGANISM: Artificial
<220> FEATURE:
<223> OTHER INFORMATION: Antibody AT10-004 and AT10-004 mutants

<400> SEQUENCE: 45
gatgcatcca acagggccac t                                          21

<210> SEQ ID NO 46
<211> LENGTH: 24
<212> TYPE: DNA
<213> ORGANISM: Artificial
<220> FEATURE:
<223> OTHER INFORMATION: Antibody AT10-004 and AT10-004 mutants

<400> SEQUENCE: 46
cagcagcgtt acaactggct taag                                       24

<210> SEQ ID NO 47
<211> LENGTH: 384
<212> TYPE: DNA
<213> ORGANISM: Artificial
<220> FEATURE:
<223> OTHER INFORMATION: Antibody AT10-004 and AT10-004 mutants

<400> SEQUENCE: 47
caggttcagc tggtgcagtc tggagctgag gtgaggaagc ctggggcctc agtgaaggtc    60
tcctgcaagg cttccggtta cacgtttacc aggcatggta tcagctgggt gcgacaggcc   120
cctggacaag gcttgagtg gatgggatgg atcagcgctt acactggtga cacagactat    180
gcacagaaat tccaggggcg agtcaccatg accacagata catccacgaa cacagcctac   240
atggaactga ggagcctgag atctgacgac gcggccgtat attactgtgc gagacttcgt   300
ttgcagggtg aagtggtggt ccctcctagt caatccaatt ggttcgaccc ctggggccag   360
ggaaccctgg tcaccgtctc ctca                                          384

<210> SEQ ID NO 48
<211> LENGTH: 333
<212> TYPE: DNA
<213> ORGANISM: Artificial
<220> FEATURE:
<223> OTHER INFORMATION: Antibody AT10-004 and AT10-004 mutants

<400> SEQUENCE: 48
gaaattgtgt tgacacagtc tccagccacc ctgtctttgt atccagggga aagagccacc    60
ctctcttgca gggccagtca gagtgttagc aggtacttag cctggtacca acagaaacct   120
ggccaggctc ccaggctcct catctatgat gcatccaaca gggccactgg catcccagcc   180
aggttcagtg gcagtgggtc tgggacagac ttcacccctca ccatcagcac gctagagcct   240
gaagattttg cagtttatta ctgtcagcag cgttacaact ggcttaagat cacccttcggc   300 caagggacac gactggaaat taaaggaact gtg                                333

<210> SEQ ID NO 49
<211> LENGTH: 5
<212> TYPE: PRT
<213> ORGANISM: Artificial
<220> FEATURE:
<223> OTHER INFORMATION: Synthetic Construct

<400> SEQUENCE: 49

Arg His Gly Ile Ser
1               5

<210> SEQ ID NO 50
<211> LENGTH: 17
<212> TYPE: PRT
<213> ORGANISM: Artificial
<220> FEATURE:
<223> OTHER INFORMATION: Synthetic Construct

<400> SEQUENCE: 50

Trp Ile Ser Ala Tyr Thr Gly Asp Thr Asp Tyr Ala Gln Lys Phe Gln
1               5                   10                  15

Gly

<210> SEQ ID NO 51
<211> LENGTH: 19
<212> TYPE: PRT
<213> ORGANISM: Artificial
<220> FEATURE:
<223> OTHER INFORMATION: Synthetic Construct

<400> SEQUENCE: 51

Leu Arg Leu Gln Gly Glu Val Val Pro Pro Ser Gln Ser Asn Trp
1               5                   10                  15

Phe Asp Pro

<210> SEQ ID NO 52
<211> LENGTH: 11
<212> TYPE: PRT
<213> ORGANISM: Artificial
<220> FEATURE:
<223> OTHER INFORMATION: Synthetic Construct

<400> SEQUENCE: 52

Arg Ala Ser Gln Ser Val Ser Arg Phe Leu Ala
1               5                   10

<210> SEQ ID NO 53
<211> LENGTH: 7
<212> TYPE: PRT
<213> ORGANISM: Artificial
<220> FEATURE:
<223> OTHER INFORMATION: Synthetic Construct

<400> SEQUENCE: 53

Asp Ala Ser Asn Arg Ala Thr
1               5

<210> SEQ ID NO 54
<211> LENGTH: 8
<212> TYPE: PRT
<213> ORGANISM: Artificial
<220> FEATURE:
<223> OTHER INFORMATION: Synthetic Construct

<400> SEQUENCE: 54

Gln Gln Arg Tyr Asn Trp Leu Lys
1               5

<210> SEQ ID NO 55
<211> LENGTH: 128
<212> TYPE: PRT
<213> ORGANISM: Artificial

<220> FEATURE:
<223> OTHER INFORMATION: Synthetic Construct

<400> SEQUENCE: 55

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Arg His
                20                  25                  30

Gly Ile Ser Trp Val Arg Gln Ala Pro Gly Gln Gly Leu Glu Trp Met
            35                  40                  45

Gly Trp Ile Ser Ala Tyr Thr Gly Asp Thr Asp Tyr Ala Gln Lys Phe
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Asp Ala Ala Val Tyr Tyr Cys
                85                  90                  95

Ala Arg Leu Arg Leu Gln Gly Glu Val Val Val Pro Pro Ser Gln Ser
            100                 105                 110

Asn Trp Phe Asp Pro Trp Gly Gln Gly Thr Leu Val Thr Val Ser Ser
        115                 120                 125

<210> SEQ ID NO 56
<211> LENGTH: 111
<212> TYPE: PRT
<213> ORGANISM: Artificial
<220> FEATURE:
<223> OTHER INFORMATION: Synthetic Construct

<400> SEQUENCE: 56

Glu Ile Val Leu Thr Gln Ser Pro Ala Thr Leu Ser Leu Tyr Pro Gly
1               5                   10                  15

Glu Arg Ala Thr Leu Ser Cys Arg Ala Ser Gln Ser Val Ser Arg Phe
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Tyr Asn Trp Leu Lys
                85                  90                  95

Ile Thr Phe Gly Gln Gly Thr Arg Leu Glu Ile Lys Gly Thr Val
            100                 105                 110

<210> SEQ ID NO 57
<211> LENGTH: 15
<212> TYPE: DNA
<213> ORGANISM: Artificial
<220> FEATURE:
<223> OTHER INFORMATION: Antibody AT10-004 and AT10-004 mutants

<400> SEQUENCE: 57
aggcatggta tcagc                                                15

<210> SEQ ID NO 58
<211> LENGTH: 51
<212> TYPE: DNA
<213> ORGANISM: Artificial
<220> FEATURE:
<223> OTHER INFORMATION: Antibody AT10-004 and AT10-004 mutants

<400> SEQUENCE: 58
tggatcagcg cttacactgg tgacacagac tatgcacaga aattccaggg g                51

<210> SEQ ID NO 59
<211> LENGTH: 57
<212> TYPE: DNA
<213> ORGANISM: Artificial
<220> FEATURE:
<223> OTHER INFORMATION: Antibody AT10-004 and AT10-004 mutants

<400> SEQUENCE: 59
cttcgtttgc agggtgaagt ggtggtccct cctagtcaat ccaattggtt cgacccc        57

<210> SEQ ID NO 60
<211> LENGTH: 33
<212> TYPE: DNA
<213> ORGANISM: Artificial
<220> FEATURE:
<223> OTHER INFORMATION: Antibody AT10-004 and AT10-004 mutants

<400> SEQUENCE: 60
agggccagtc agagtgttag caggttctta gcc                                  33

<210> SEQ ID NO 61
<211> LENGTH: 21
<212> TYPE: DNA
<213> ORGANISM: Artificial
<220> FEATURE:
<223> OTHER INFORMATION: Antibody AT10-004 and AT10-004 mutants

<400> SEQUENCE: 61
gatgcatcca acagggccac t                                               21

<210> SEQ ID NO 62
<211> LENGTH: 24
<212> TYPE: DNA
<213> ORGANISM: Artificial
<220> FEATURE:
<223> OTHER INFORMATION: Antibody AT10-004 and AT10-004 mutants

<400> SEQUENCE: 62
cagcagcgtt acaactggct taag                                            24

<210> SEQ ID NO 63
<211> LENGTH: 384
<212> TYPE: DNA
<213> ORGANISM: Artificial
<220> FEATURE:
<223> OTHER INFORMATION: Antibody AT10-004 and AT10-004 mutants

<400> SEQUENCE: 63
caggttcagc tggtgcagtc tggagctgag gtgaggaagc ctggggcctc agtgaaggtc      60
tcctgcaagg cttccggtta cacgtttacc aggcatggta tcagctgggt ggcacaggcc     120
cctggacaag gcttgagtg gatgggatgg atcagcgctt acactggtga cacagactat     180
gcacagaaat tccagggcg agtcaccatg accacagata catccacgaa cacagcctac     240
atggaactga ggagcctgag atctgacgac gcggccgtat attactgtgc gagacttcgt     300
ttgcagggtg aagtggtggt ccctcctagt caatccaatt ggttcgaccc ctggggccag     360
ggaaccctgg tcaccgtctc ctca                                           384

```
<210> SEQ ID NO 64
<211> LENGTH: 342
<212> TYPE: DNA
<213> ORGANISM: Artificial
<220> FEATURE:
<223> OTHER INFORMATION: Antibody AT10-004 and AT10-004 mutants

<400> SEQUENCE: 64
gaaattgtgt tgacacagtc tccagccacc ctgtctttgt atccagggga aagagccacc      60
ctctcttgca gggccagtca gagtgttagc aggttcttag cctggtacca acagaaacct     120
ggccaggctc ccaggctcct catctatgat gcatccaaca gggccactgg catcccagcc     180
aggttcagtg gcagtgggtc tgggacagac ttcaccctca ccatcagcag cctagagcct     240
gaagattttg cagttttttgc agtttattac tgtcagcagc gttacaactg gcttaagatc     300
accttcggcc aagggacacg actggaaatt aaaggaactg tg                        342
```